(12) United States Patent
Dhatt et al.

(10) Patent No.: US 12,743,774 B2
(45) Date of Patent: Sep. 22, 2026

(54) CONTEXTUAL PROCESSING OF ULTRASOUND DATA

(71) Applicant: FUJIFILM SONOSITE, INC., Bothell, WA (US)

(72) Inventors: Davin Dhatt, Woodinville, WA (US); David Knapp, Bellevue, WA (US); Christopher Howard, Seattle, WA (US); Kristine Kelly, San Diego, CA (US); Thomas Endres, Sagle, ID (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 278 days.

(21) Appl. No.: 18/479,881

(22) Filed: Oct. 3, 2023

(65) Prior Publication Data

US 2025/0111501 A1 Apr. 3, 2025

(51) Int. Cl.
*G06T 7/00* (2017.01)
*A61B 8/00* (2006.01)
(Continued)

(52) U.S. Cl.
CPC .......... *G06T 7/0012* (2013.01); *A61B 8/5207* (2013.01); *G06T 7/11* (2017.01); *G16H 10/60* (2018.01); *G16H 15/00* (2018.01); *G16H 20/00* (2018.01); *G16H 30/40* (2018.01); *G16H 50/30* (2018.01); *G06T 2207/10016* (2013.01); *G06T 2207/10132* (2013.01); *G06T 2207/20084* (2013.01)

(58) Field of Classification Search
CPC ..................... G06T 7/0012; G06T 7/11; G06T 2207/10016; G06T 2207/10132; G06T 2207/20084; G16H 10/60; G16H 15/00; G16H 50/30; G16H 20/00; G16H 30/40; A61B 8/5207
See application file for complete search history.

(56) References Cited

U.S. PATENT DOCUMENTS 11,205,520 B1 12/2021 Irani
11,869,188 B1 * 1/2024 Levy .................... A61B 8/0883
(Continued)

FOREIGN PATENT DOCUMENTS

EP 3964136 A1 * 3/2022 ........... A61B 8/0883

OTHER PUBLICATIONS

NPL: IP.com and IEEE, Results Publication Date Range: Oct. 29, 2009 to Dec. 11, 2025.*
(Continued)

*Primary Examiner* — Quang N Vo
(74) *Attorney, Agent, or Firm* — Womble Bond Dickinson (US) LLP

(57) ABSTRACT

An ultrasound system includes an ultrasound scanner configured to transmit ultrasound at a patient anatomy and generate ultrasound data as part of an ultrasound examination. The ultrasound system also includes an ultrasound machine configured to generate, based on the ultrasound data, an ultrasound image. The ultrasound system also includes a processor system implemented to determine features selected from the group consisting of regional features, patient features, clinician features, and ultrasound examination feature. The processor system is implemented to generate, based on the ultrasound image and the features, a patient recommendation.

20 Claims, 16 Drawing Sheets

(51) Int. Cl.

| | |
|---|---|
| ***A61B 8/08*** | (2006.01) |
| ***G06T 7/11*** | (2017.01) |
| ***G16H 10/60*** | (2018.01) |
| ***G16H 15/00*** | (2018.01) |
| ***G16H 20/00*** | (2018.01) |
| ***G16H 30/40*** | (2018.01) |
| ***G16H 50/30*** | (2018.01) |

(56) References Cited

U.S. PATENT DOCUMENTS

2021/0027485 A1 1/2021 Zhang
2021/0345987 A1 * 11/2021 Ciofolo-Veit .......... A61B 8/466

OTHER PUBLICATIONS

Non-Final Office Action received in related U.S. Appl. No. 18/523,598, mailed Mar. 11, 2026, 13 pages.

* cited by examiner

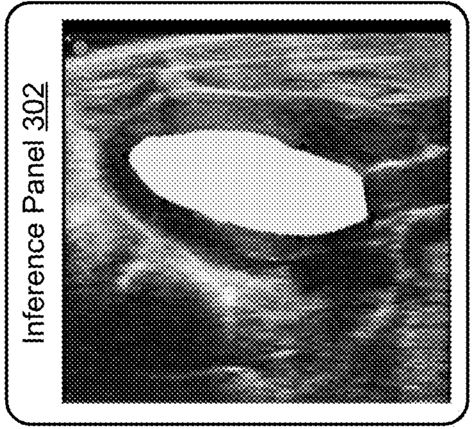
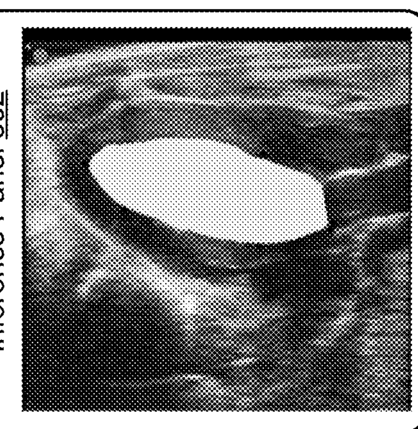
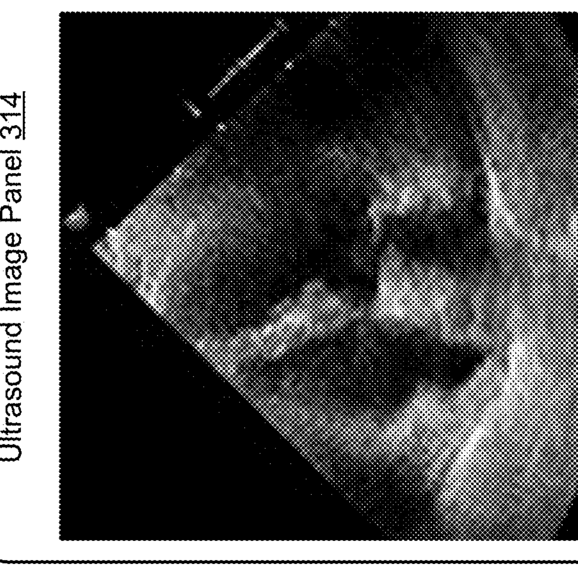
FIG. 3

Figure 8:
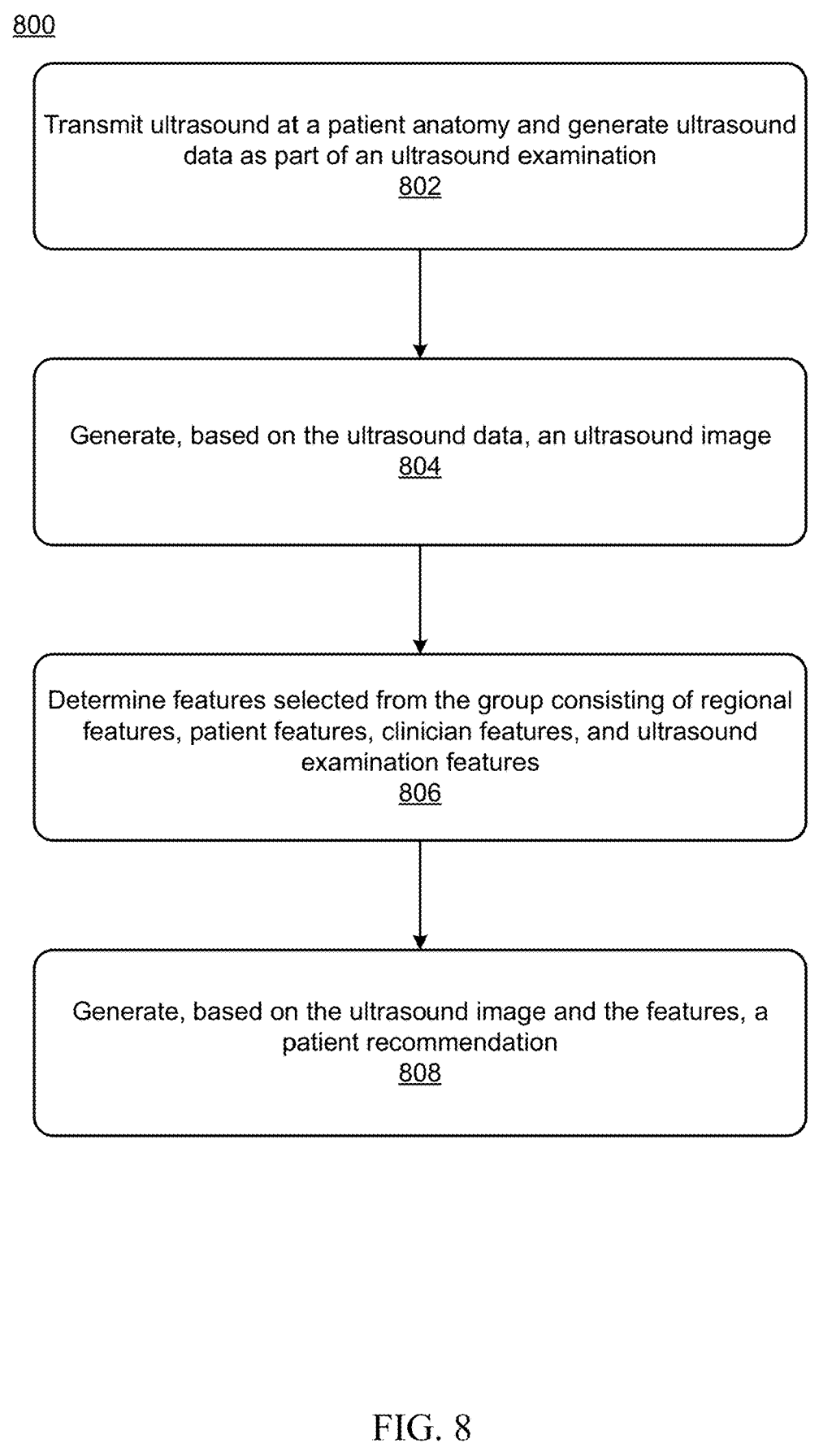

800

Transmit ultrasound at a patient anatomy and generate ultrasound data as part of an ultrasound examination
802

Generate, based on the ultrasound data, an ultrasound image
804

Determine features selected from the group consisting of regional features, patient features, clinician features, and ultrasound examination features
806

Generate, based on the ultrasound image and the features, a patient recommendation
808

Figure 9:
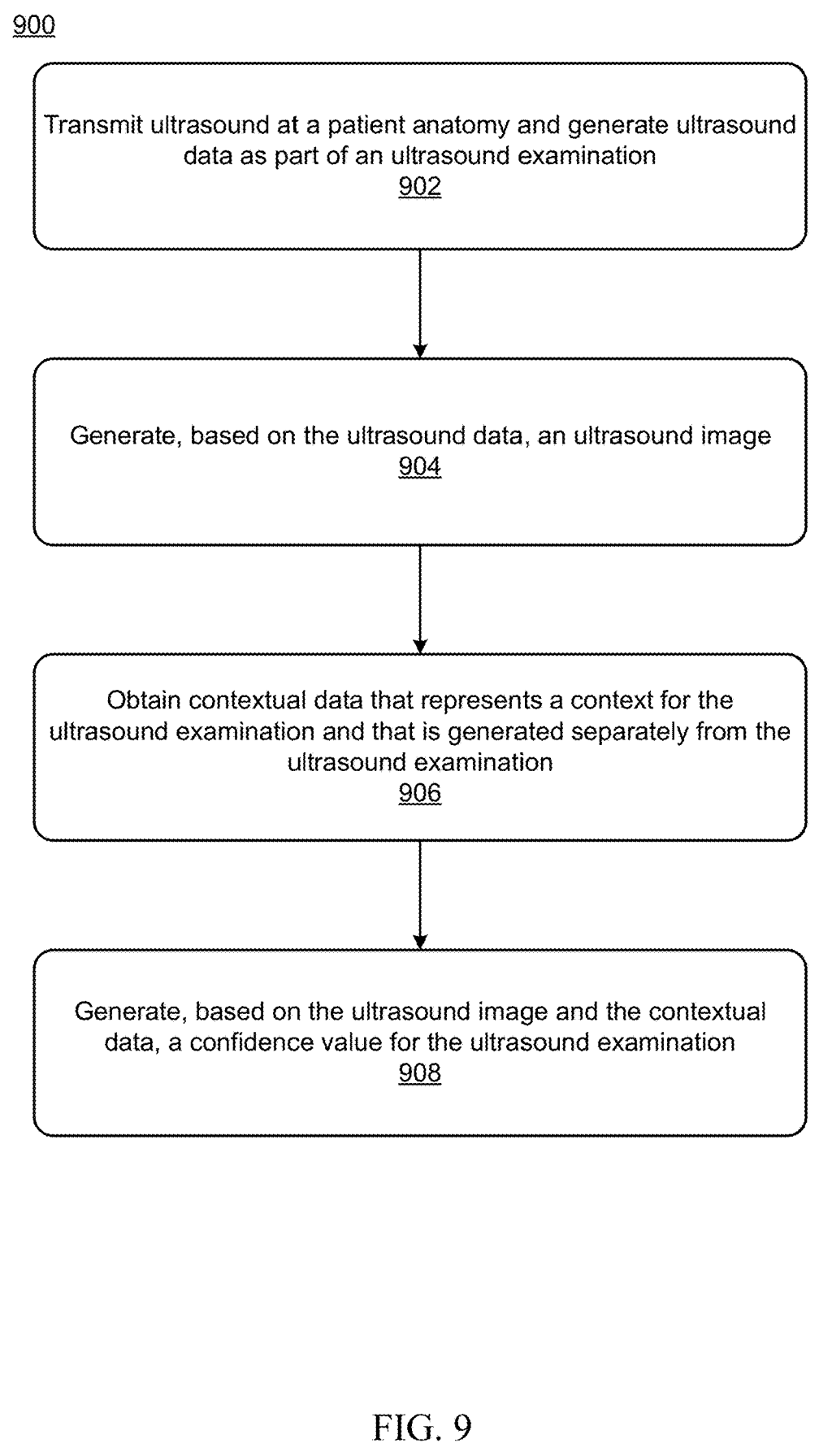

Transmit ultrasound at a patient anatomy and generate ultrasound data as part of an ultrasound examination
902

Generate, based on the ultrasound data, an ultrasound image
904

Obtain contextual data that represents a context for the ultrasound examination and that is generated separately from the ultrasound examination
906

Generate, based on the ultrasound image and the contextual data, a confidence value for the ultrasound examination
908

Figure 10:
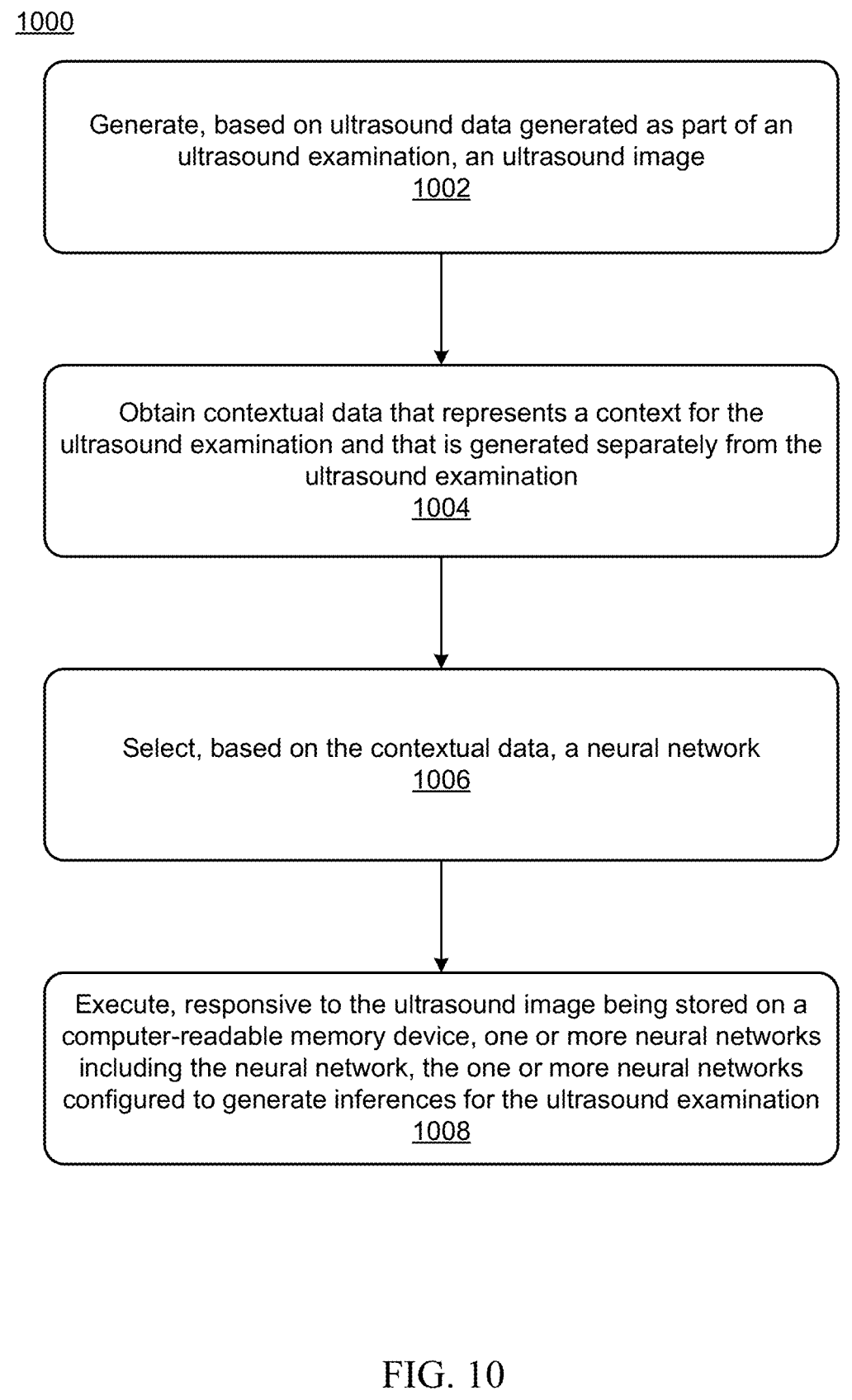

Generate, based on ultrasound data generated as part of an ultrasound examination, an ultrasound image
1002

Obtain contextual data that represents a context for the ultrasound examination and that is generated separately from the ultrasound examination
1004

Select, based on the contextual data, a neural network
1006

Execute, responsive to the ultrasound image being stored on a computer-readable memory device, one or more neural networks including the neural network, the one or more neural networks configured to generate inferences for the ultrasound examination
1008

Figure 11:
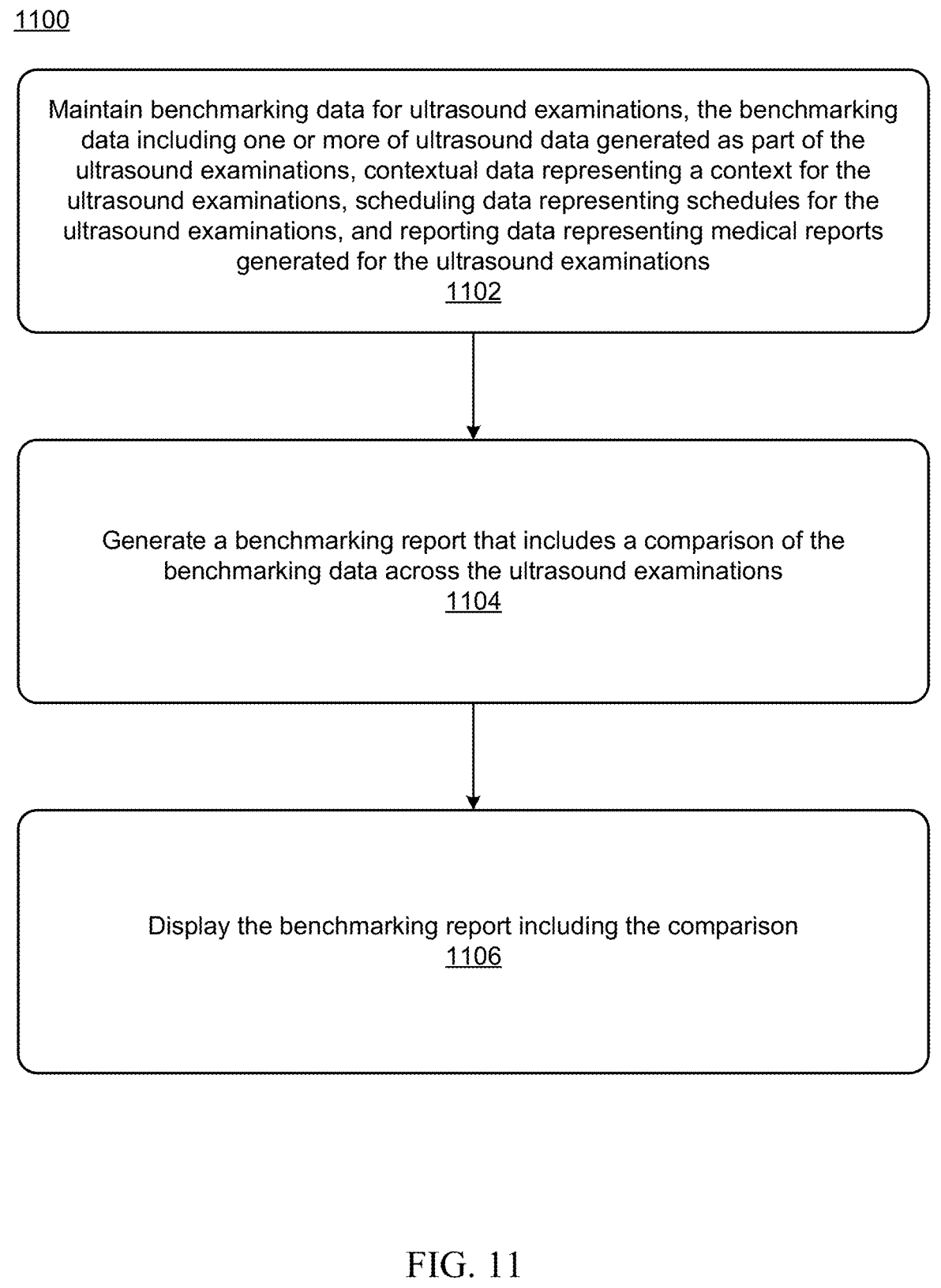

Maintain benchmarking data for ultrasound examinations, the benchmarking data including one or more of ultrasound data generated as part of the ultrasound examinations, contextual data representing a context for the ultrasound examinations, scheduling data representing schedules for the ultrasound examinations, and reporting data representing medical reports generated for the ultrasound examinations
1102

Generate a benchmarking report that includes a comparison of the benchmarking data across the ultrasound examinations
1104

Display the benchmarking report including the comparison
1106

Figure 12:
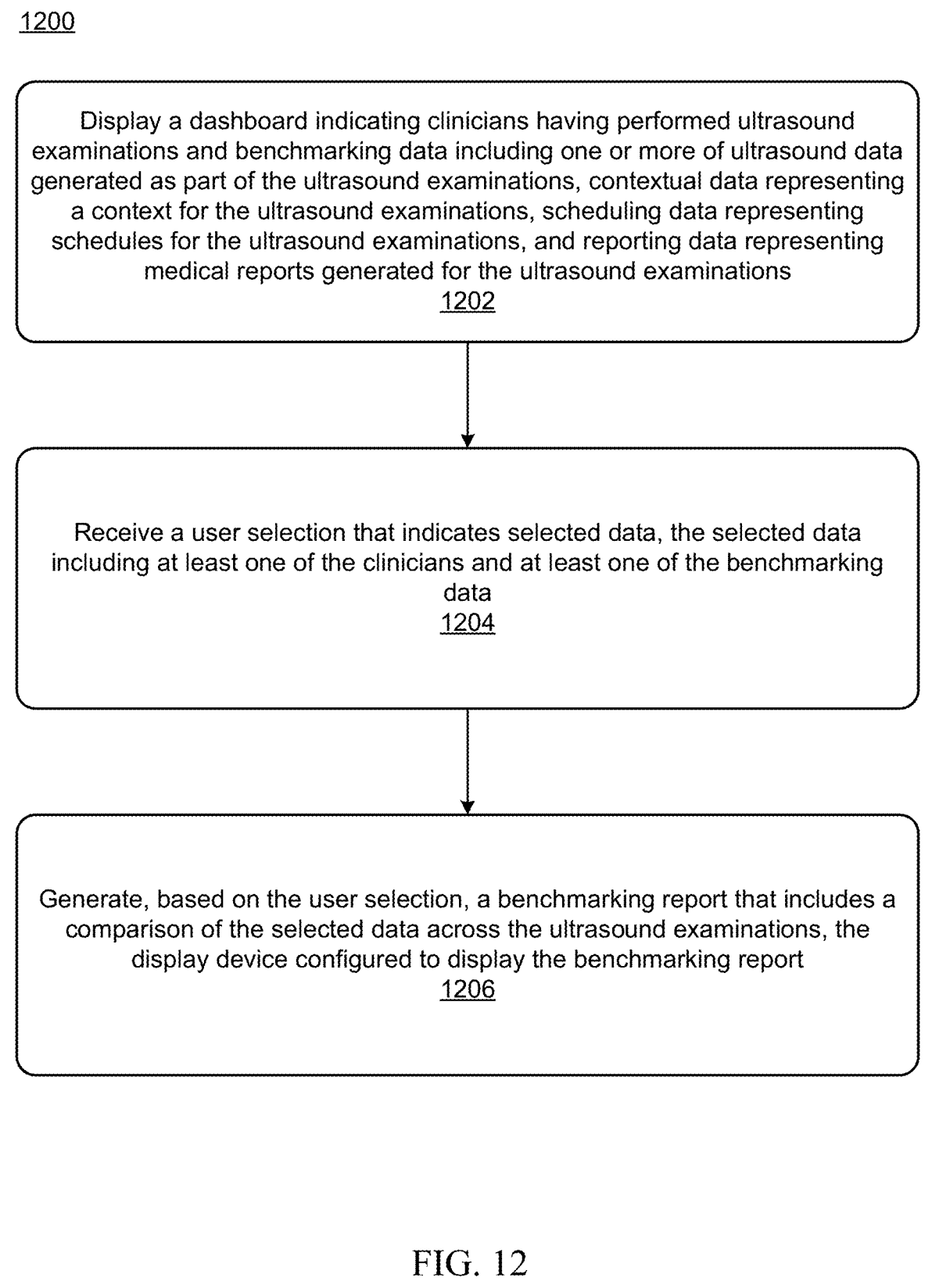

Display a dashboard indicating clinicians having performed ultrasound examinations and benchmarking data including one or more of ultrasound data generated as part of the ultrasound examinations, contextual data representing a context for the ultrasound examinations, scheduling data representing schedules for the ultrasound examinations, and reporting data representing medical reports generated for the ultrasound examinations
1202

Receive a user selection that indicates selected data, the selected data including at least one of the clinicians and at least one of the benchmarking data
1204

Generate, based on the user selection, a benchmarking report that includes a comparison of the selected data across the ultrasound examinations, the display device configured to display the benchmarking report
1206

Figure 13:
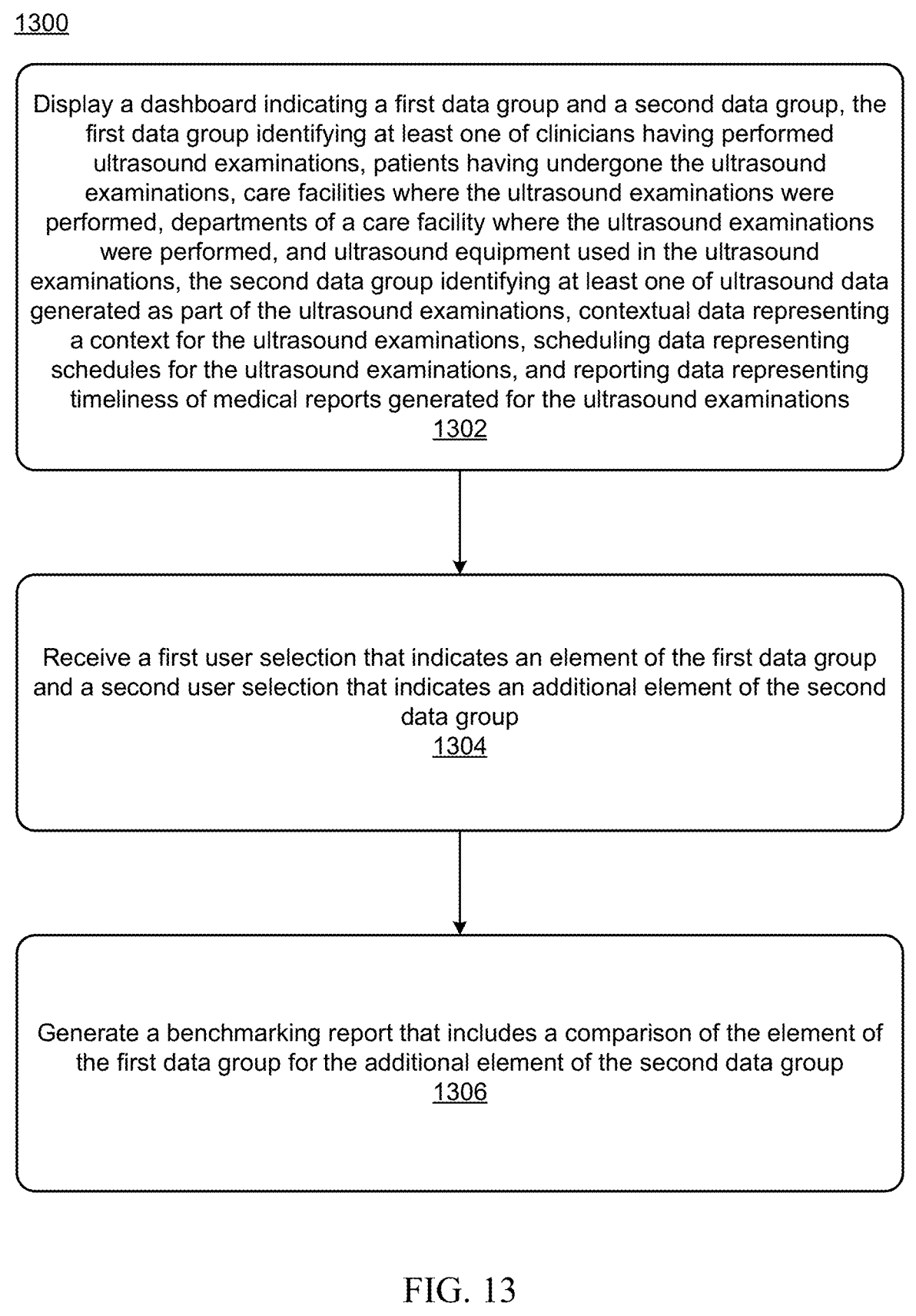

Display a dashboard indicating a first data group and a second data group, the first data group identifying at least one of clinicians having performed ultrasound examinations, patients having undergone the ultrasound examinations, care facilities where the ultrasound examinations were performed, departments of a care facility where the ultrasound examinations were performed, and ultrasound equipment used in the ultrasound examinations, the second data group identifying at least one of ultrasound data generated as part of the ultrasound examinations, contextual data representing a context for the ultrasound examinations, scheduling data representing schedules for the ultrasound examinations, and reporting data representing timeliness of medical reports generated for the ultrasound examinations
1302

Receive a first user selection that indicates an element of the first data group and a second user selection that indicates an additional element of the second data group
1304

Generate a benchmarking report that includes a comparison of the element of the first data group for the additional element of the second data group
1306

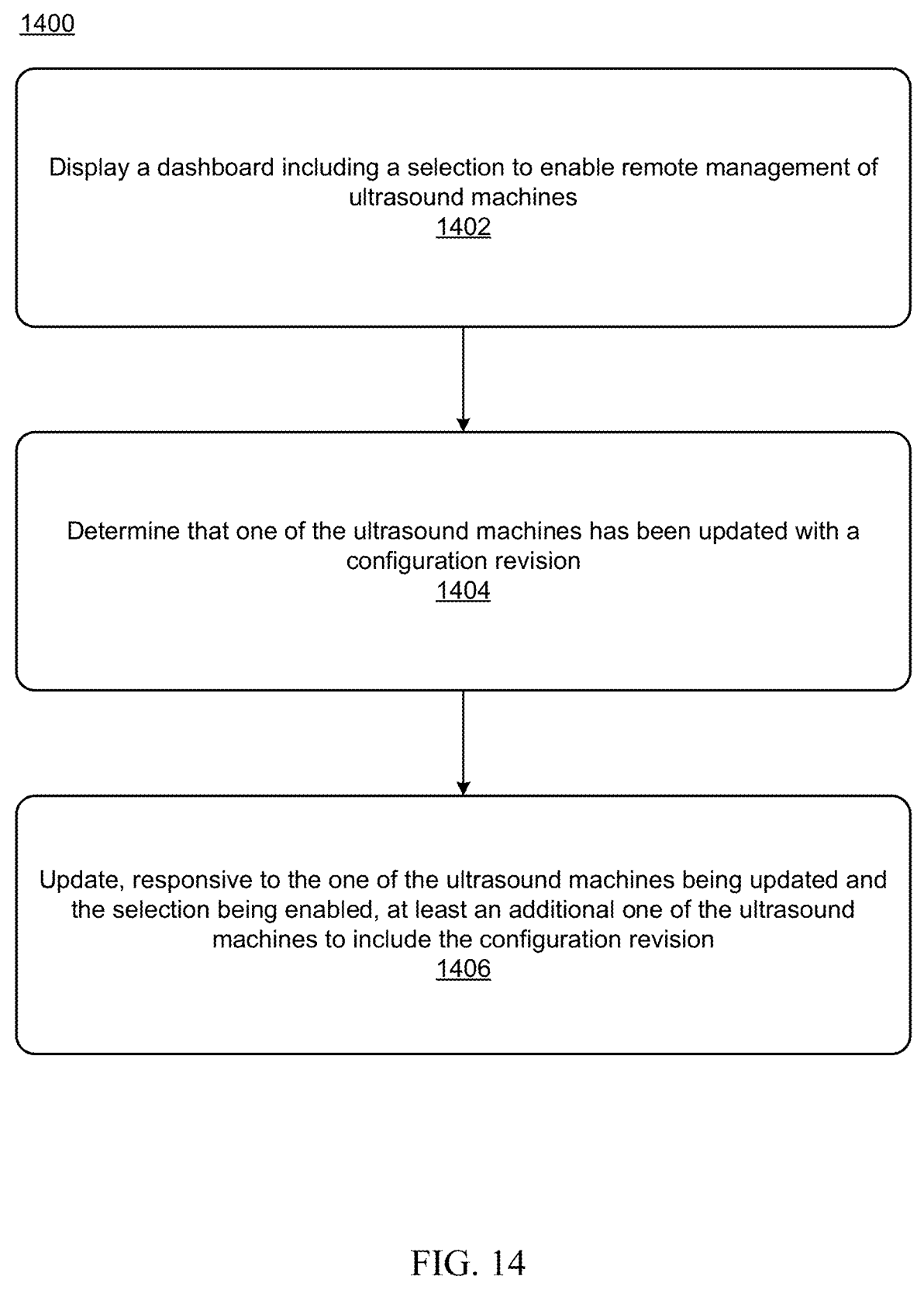

Display a dashboard including a selection to enable remote management of ultrasound machines
1402

Determine that one of the ultrasound machines has been updated with a configuration revision
1404

Update, responsive to the one of the ultrasound machines being updated and the selection being enabled, at least an additional one of the ultrasound machines to include the configuration revision
1406

FIG. 14

CONTEXTUAL PROCESSING OF ULTRASOUND DATA

Embodiments disclosed herein relate to ultrasound systems. More specifically, embodiments disclosed herein relate to contextual processing of ultrasound data.

BACKGROUND

Ultrasound systems can generate ultrasound images by transmitting sound waves at frequencies above the audible spectrum into a body, receiving echo signals caused by the sound waves reflecting from internal body parts, and converting the echo signals into electrical signals for image generation. Because they are non-invasive and non-ionizing, ultrasound systems are used ubiquitously. For instance, ultrasound systems are often used at the point of care, such as in an emergency department of a hospital, at a patient's bedside, on the battlefield, and the like.

However, most ultrasound examinations are constrained to utilizing data captured during the ultrasound examination, such as with an ultrasound system. The examination is thus study-centric. Hence, ultrasound examinations often lack context, including a basis of comparison for interpreting the ultrasound results. Moreover, ultrasound examinations, especially point-of-care ultrasound examinations, are subject to little or no quality assurance outside the examination. Accordingly, conventional ultrasound systems and their use may not result in the best possible patient care.

SUMMARY

Systems and methods for contextual processing of ultrasound data are described. In some embodiments, an ultrasound system includes an ultrasound scanner configured to transmit ultrasound at a patient anatomy and generate ultrasound data as part of an ultrasound examination. The ultrasound system also includes an ultrasound machine configured to generate, based on the ultrasound data, an ultrasound image. The ultrasound system further includes a processor system implemented to determine features selected from the group consisting of regional features, patient features, clinician features, and ultrasound examination features, and generate, based on the ultrasound image and the features, a patient recommendation.

In some other embodiments, an ultrasound system includes an ultrasound scanner configured to transmit ultrasound at a patient anatomy and generate ultrasound data as part of an ultrasound examination. The ultrasound system also includes an ultrasound machine configured to generate, based on the ultrasound data, an ultrasound image. The ultrasound system further includes a processor system implemented to obtain contextual data that represents a context for the ultrasound examination and that is generated separately from the ultrasound examination. The processor system is also implemented to generate, based on the ultrasound image and the contextual data, a confidence value for the ultrasound examination.

In yet some other embodiments, an ultrasound system includes an ultrasound machine configured to generate, based on ultrasound data generated as part of an ultrasound examination, an ultrasound image. The ultrasound system also includes a computer-readable memory device and a processor system implemented to obtain contextual data that represents a context for the ultrasound examination and that is generated separately from the ultrasound examination The processor system is also implemented to select, based on the contextual data, a neural network and execute, responsive to the ultrasound image being stored on the computer-readable memory device, one or more neural networks including the neural network. The one or more neural networks are configured to generate inferences for the ultrasound examination.

Other systems, devices, and methods related to contextual processing of ultrasound data are also described.

BRIEF DESCRIPTION OF THE DRAWINGS

The appended drawings illustrate examples and are, therefore, exemplary embodiments and not considered to be limiting in scope.

FIG. 3 illustrates an example dashboard for contextual processing of ultrasound data in accordance with some embodiments.

FIG. 8 illustrates an example method that can be implemented by an ultrasound system in accordance with some embodiments.

FIG. 9 illustrates an example method that can be implemented by an ultrasound system in accordance with some embodiments.

FIG. 10 illustrates an example method that can be implemented by an ultrasound system in accordance with some embodiments.

FIG. 11 illustrates an example method that can be implemented by an ultrasound system in accordance with some embodiments.

FIG. 12 illustrates an example method that can be implemented by an ultrasound system in accordance with some embodiments.

FIG. 13 illustrates an example method that can be implemented by an ultrasound system in accordance with some embodiments.

FIG. 14 illustrates an example method that can be implemented by an ultrasound system in accordance with some embodiments.

DETAILED DESCRIPTION

Figure 1:
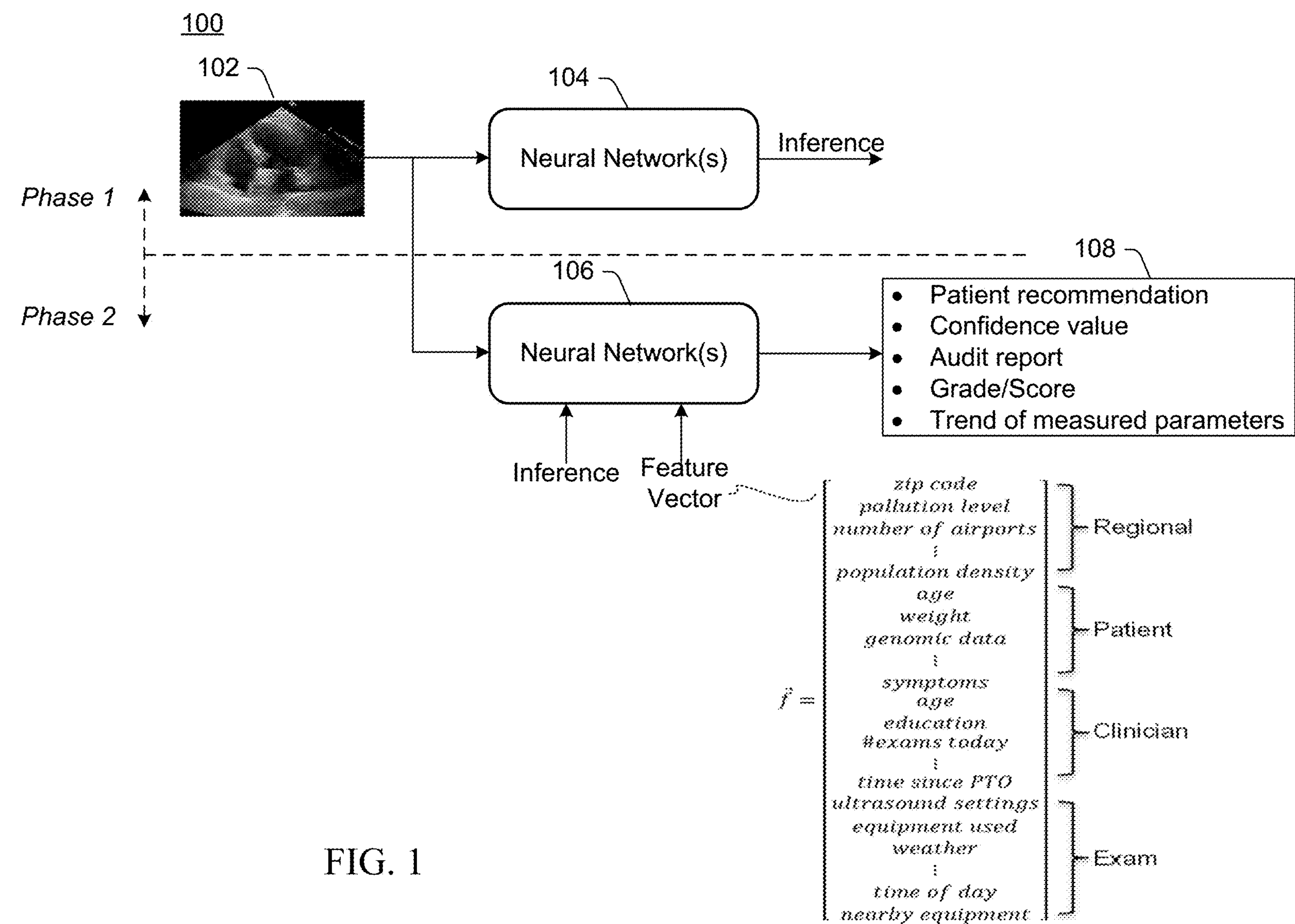
FIG. 1 depicts a view illustrating a system for contextual processing of ultrasound data in accordance with some embodiments.

In the following description, numerous details are set forth to provide a more thorough explanation of embodiments of the present invention. It will be apparent, however, to one skilled in the art, that the embodiments of the present invention may be practiced without these specific details. In other instances, well-known structures and devices are shown in block diagram form, rather than in detail, in order to avoid obscuring embodiments of the present invention.

Conventional ultrasound systems can be constrained to utilizing data captured during the ultrasound examination, and are study-centric, rather than patient-centric. For instance, an ultrasound operator (e.g., clinician or sonographer) may not have access to a patient's history during an ultrasound examination. Moreover, ultrasound examinations often lack context, including a basis of comparison for interpreting the ultrasound results. For instance, conventional ultrasound examinations do not account for contextual data that can affect a patient during an ultrasound examination. As an example, a patient can be affected by current events, such as by having higher blood pressure than usual on Sep. 11, 2001 due to the catastrophic events of that day. As another example, an ultrasound system itself can be affected by current events, such as radio frequency (RF) interference that can occur intermittently. Hence, conventional ultrasound systems and their use may not result in the best possible patient care.

Accordingly, systems, devices, and techniques are disclosed herein for contextual processing of ultrasound data. In some embodiments, contextual processing of ultrasound data occurs during an ultrasound examination. Additionally or alternatively, contextual processing of ultrasound data can occur subsequent to an ultrasound examination in which the ultrasound data is generated. An ultrasound system in accordance with an embodiment of the present invention can determine features representing contextual data and construct a feature vector. Examples of features representing contextual data include regional features (e.g., features specific to a region or location where an examination is performed or where a patient resides, such as an amount of pollution in a city, population density, etc.). Examples of features representing contextual data can also include patient features (e.g., patient age, patient ethnicity, patient genomic data, etc.), clinician features (e.g., education level, time since a last vacation, number of examinations previously performed, etc.), and examination features (e.g., data regarding ultrasound equipment used, calibration and/or cleaning data, a measure of RF interference during an examination, etc.). The ultrasound system can include one or more machine-learned models (e.g., neural networks) and process ultrasound data (e.g., an ultrasound image and/or an inference, such as a segmentation, classification, etc.) and condition the ultrasound data with the feature vector. That is, the neural network can receive the feature vector as a secondary or additional input to uncover hidden correlations between the features and the ultrasound data. In some embodiments, the neural network can generate outputs conditioned on context, including recommendations (e.g., recommendations for patient care), a grade or score for an ultrasound examination, an ultrasound image, or a clinician, a confidence value for a result of an ultrasound examination, an audit report that compares an ultrasound examination with other ultrasound examinations, an alert, and the like.

Moreover, the ultrasound system can access stored data, such as from a medical archiver system, and display results of a previous ultrasound examination concurrently with results of a current ultrasound examination. In some embodiments, the ultrasound system can generate a composite image (e.g., a 3D image) or a video by combining previous and current ultrasound data. In an example, the ultrasound system can synchronize display of current and previous clips, e.g., to phase lock heartbeat cycles. For instance, the ultrasound system can overlay a previous segmentation of a patient anatomy with a current segmentation of the patient anatomy to show the change in the patient anatomy since the previous examination. Hence, the ultrasound system can be used for a patient-centric examination and is not limited to a study-centric examination. Accordingly, the ultrasound examination can provide better patient care than conventional ultrasound systems.

FIG. 1 is a view 100 illustrating a system for contextual processing of ultrasound data in accordance with some embodiments. As shown in FIG. 1, the system includes an ultrasound image 102 that can be generated by any suitable ultrasound system as part of an ultrasound examination. The ultrasound image 102 can include any suitable type of ultrasound image, such as a B-mode image, an M-mode image, a C-mode image, a video clip, etc. The system also includes one or more neural networks 104 that can generate an inference based on the ultrasound image 102. Examples of an inference that can be generated by the neural network 104 include, but are not limited to, a segmentation of an object (e.g., a patient anatomy in the ultrasound image 102), a classification of an object, a detection of an object, a probability (e.g., a probability that an object is included in the ultrasound image or that a property of the object, such as its size, is greater than a threshold), a measurement (e.g., a distance), a prediction, and the like. Generally, the inference can include any suitable measurement, detection, observation, or prediction generated based on the ultrasound image 102. The ultrasound image 102 and the inference generated by the neural network 104 can occur as part of "phase 1" of the operation of the system. Phase 1 can occur during an ultrasound examination. Additionally or alternatively, phase 1 can occur after an ultrasound examination in which the ultrasound image 102 is generated.

As part of "phase 2" of the operation of the system, the ultrasound image 102 is processed by one or more neural networks 106 that also receive one or more additional or secondary inputs, including the inference generated by the neural network 104 and/or a feature vector that includes features representing contextual data for the ultrasound examination. In some embodiments, the features/contextual data can represent a context for the ultrasound examination and be generated separately from the ultrasound examination (e.g., independently from the ultrasound examination). For example, the features/contextual data can be generated in another part of the care facility where the ultrasound examination is performed or even by an entity unrelated to the care facility. The feature vector can include, but is not limited to, operator history data, data from the hospital on a same day of the examination, non-examination data, data from the same operator for a different patient, and/or patient data from a previous examination. The feature vector can include, but is not limited to, regional features, patient features, clinician features, and examination features.

In some embodiments, regional features include contextual data that represents a region, area, or location where the ultrasound examination is performed and/or where a patient resides. The region can include a city, county, community, neighborhood, state, province, island, etc. Examples of regional features can include a population size, a population density, a pollution level (e.g., measure of particulate levels in air and/or water), a number of airports in the region, a measure of traffic (e.g., average number of vehicles on the road in a day), traffic density (e.g., number of registered vehicles normalized per square mile), and the like. Additionally or alternatively, regional features can include statistics representing ethnicity, age, political bias, types of flora and fauna, etc. in the region. Additionally or alternatively, regional features can include one or more zip codes representing the region, an area code representing telephone coverage in the region, map coordinates, latitude and longitude, GPS coordinates, and other suitable alphanumeric codes designating a region. In some embodiments, the regional features include regional news events, weather (e.g., average temperature, number of sunny days, amount of rainfall, etc.), known disorders associated with the region (e.g., autism, multiple sclerosis, or depression can be associated with regions having limited sunlight), and the like.

In some embodiments, patient features include contextual data that represents the patient undergoing the ultrasound examination. Examples of patient features can include a patient age, a patient weight, a symptom description, patient genomic data, family history, a patient medical history, history of residences, military history, etc. Additionally or alternatively, the patient features can include a patient ethnicity, religion, political affiliation, patient preferences (e.g., likes and dislikes), employment type and/or status, marriage status, education level and/or type, etc. Additionally or alternatively, the patient features can include patient data from a previous or future ultrasound examination. For example, phase 2 of the operation of the system can be performed subsequent to an ultrasound examination performed during phase 1, so that the feature vector can include features/contextual data that are unavailable during the ultrasound examination simply because they have not yet been generated relative to phase 1 and/or the ultrasound examination in which the ultrasound image 102 is generated.

In some embodiments, clinician features include contextual data that represents one or more clinicians (e.g., sonographer or operator) performing the ultrasound examination. Examples of clinician features can include a clinician age, an education level, an education history (e.g., degrees earned and universities issuing the degrees), military history, board certification status, job title, number and description of hospitals and care facilities the clinician currently works and/or previously worked, and the like. Additionally or alternatively, the clinician features can include a number of ultrasound examinations performed by the clinician in total (e.g., as a clinician), a number of ultrasound examinations performed by the clinician on the day of the ultrasound examination (of phase 1), an amount of time since the clinician's last vacation, an amount of time since the clinician's last break in the day of the ultrasound examination, a number of scheduled examinations for the clinician already performed and/or scheduled to be performed for the day, etc. Additionally or alternatively, the clinician features can include a marital status for the clinician, ultrasound data generated by the clinician for another patient than the patient undergoing the ultrasound examination of phase 1, and the like.

In some embodiments, examination features (also referred to as ultrasound examination features) include contextual data for the ultrasound examination that can be generated or occur concurrently with, but separately from, the ultrasound examination and/or that may be relevant to the care facility where the ultrasound examination is performed. Examples of examination features can include cleaning data for the ultrasound system, calibration data for the ultrasound system, radio frequency measurements obtained during the ultrasound examination, indicators of equipment proximate to the ultrasound system during the ultrasound examination, weather during the ultrasound examination, a time of day of the ultrasound examination, and a day of week of the ultrasound examination. Additionally or alternatively, the examination features can include data generated in the care facility where the ultrasound examination is performed, such as data generated on the same day as the ultrasound examination but in another department and/or location of the care facility. Additionally or alternatively, the examination features can include data representing the care facility where the ultrasound examination is performed, such as a list of employees working on the day of the ultrasound examination, a list of disorders treated at the care facility on the day of the ultrasound examination, and the like. The examination features can include ultrasound examination data for other ultrasound examinations than the current ultrasound examination of phase 1, performed by the same clinician as the current ultrasound examination or different clinicians.

The regional features, patient features, clinician features, and examination features described herein are examples of features that can populate the feature vector, and are not limiting. Other examples of features that can be included in the feature vector include features relating to a payer, a policy maker, a researcher, a manufacturer (e.g., drug or device manufacturer), a provider (e.g., health care provider or insurer), and the like.

As described above, since in some embodiments phase 2 is performed subsequently to phase 1 in which the current ultrasound examination can be performed, the feature vector can include some features that are unavailable during the (current) ultrasound examination. For example, some features may not have been generated at the time of the ultrasound examination. In other embodiments, phase 2 can be performed concurrently with, or immediately after, the current ultrasound examination. For example, phase 2 can be performed as part of the current ultrasound examination, so that all features of the feature vector can be available during the ultrasound examination in these other embodiments.

As part of phase 2, the neural network 106 processes the ultrasound image 102 and one or more additional or secondary inputs, including the feature vector. In an example, the additional/secondary inputs include the inference generated by the neural network 104. The neural network 106 can uncover hidden or non-obvious correlations between the contextual data of the feature vector and the ultrasound image 102 generated as part of the ultrasound examination. Accordingly, the neural network 106 can generate any suitable output 108. In some embodiments, the output 108 includes a recommendation, e.g., a patient recommendation. The patient recommendation can include a recommendation and/or scheduling of a follow-up ultrasound examination (e.g., later in the day or days or weeks to follow). The patient recommendation can include a recommendation and/or scheduling of a follow-up examination that may not include an ultrasound examination, such as a recommendation to see a cardiologist. In some embodiments, the recommendation includes a recommendation for a clinical trial. In some embodiments, the recommendation includes a recommendation for in-home care for the patient. Additionally or alternatively, the recommendation can include a recommendation for a medication, instructions for filling a prescription for the medication, and/or a method for delivery of a medication (e.g., to a patient's residence). The recommendation can include a suggested time of day, day of week, date, weather condition, clinician, ultrasound equipment manufacturer and/or model number, care facility, and the like for the patient's next ultrasound examination.

In embodiments, the output 108 includes a confidence value, such as a value between 0 and 1 indicating a confidence in the ultrasound examination. For instance, the confidence value can indicate a degree of confidence in the inference generated by the neural network 104. Additionally or alternatively, the confidence value can indicate a degree of confidence for a measurement performed by the clinician, such as a caliper measurement of distance or parameter measurement (e.g., cardiac ejection fraction). In an example, the confidence value indicates a confidence in a diagnosis based on the ultrasound image 102. Accordingly, the additional/secondary inputs to the neural network 106 can include not only the inference and the feature vector, but also any parameter, decision, etc. made during the ultrasound examination based on the ultrasound image 102, and the neural network 106 can generate a confidence value for the parameter, decision, etc. based on correlations between the parameter/decision and the feature vector. In one example, the ultrasound system is implemented to populate a dashboard with the confidence value. The dashboard can be viewable by a director of a department that manages ultrasound examinations including the ultrasound examination. An example dashboard is described below in more detail with respect to FIG. 3.

In some embodiments, the output 108 includes an audit report. The audit report can compare the current ultrasound examination and an additional ultrasound examination, such as another ultrasound examination performed by the same clinician who performs the current ultrasound examination and/or ultrasound examinations performed by other clinicians different from the clinician who performs the current ultrasound examination. Hence, the audit report can identify low-quality data relative to other data generated in a care facility, and under-performing operators/clinicians. The audit report can include strategic-level data to guarantee quality across a department, not just for a single examination.

In some embodiments, the output 108 includes a grade and/or a score. The grade/score can be included in an audit report of the output 108, and represent a clinician's overall score for an ultrasound examination. The grade/score can be based on any suitable parameter, including an amount of time it takes the clinician to perform the ultrasound examination, an amount and type of speech (e.g., conversation) between the clinician and the patient, an amount of increase in anxiety measured for the patient during the ultrasound examination, etc. In some embodiments, the grade/score represents an image quality for an ultrasound image (e.g., the ultrasound image 102) generated as part of the ultrasound examination. For instance, the grade can include a letter grade A, B, C, D, or F based on the image quality, and can be an indication of the usability of the ultrasound image, such as whether or not an ultrasound image is "good enough" to determine a pneumothorax condition.

In some embodiments, the output 108 includes a trend of measured parameters, such as a graph of a measured parameter (e.g., ejection fraction, lateral ventricles (LV) size, or other measured parameter) based on the current ultrasound examination and at least one previous ultrasound examination. The graph can be displayed in real-time during the ultrasound examination. In an example, a user can select a data point of the graph, such as a specific value of ejection fraction, and in response to the selection, the ultrasound system can display the ultrasound image from which that data point was derived. Thus, the user (e.g., clinician) can quickly navigate between ultrasound images ranging across the patient's examination history, rather than being constrained to viewing data for only the current ultrasound examination. In other words, an embodiment of the ultrasound system facilitates patient-centric ultrasound examinations and is not limited to study-centric examinations. In an example, the trend of measured parameters includes a predicted value for a parameter for a next ultrasound examination. For instance, the output 108 can include an expected value for ejection fraction for a patient's next ultrasound examination.

In some embodiments, the output 108 includes the generation of an email, such as an email to a department head or administrator who manages ultrasound examinations. Additionally or alternatively, the email can include an email to the patient and/or clinician. The email can summarize the results of the ultrasound examination and include the scheduling for a next ultrasound examination and/or a recommendation generated as part of the output 108.

In embodiments, the audit report of the output 108 can include a benchmarking report. The benchmarking report can include one or more comparisons of any suitable data. For instance, the benchmarking report can include comparisons of benchmarking data, such as ultrasound data generated as part of ultrasound examinations, contextual data representing a context for the ultrasound examinations, scheduling data representing schedules for the ultrasound examinations, reporting data representing medical reports generated for the ultrasound examinations, and the like. The benchmarking report can compare the benchmarking data across individuals, such as across clinicians and/or across patients. For instance, the benchmarking report can include a comparison across clinicians to track timeliness of ultrasound examinations performed by the clinicians, thus denoting clinicians that perform examinations on-time, early, or late relative to the scheduled times of the ultrasound examinations. Further, the benchmarking report can include a comparison across clinicians to track timeliness of medical reports for the ultrasound examinations generated and submitted to a medical records archiver by the clinicians. For example, the benchmarking report can indicate latencies relative to the time of an ultrasound examination that a clinician submits a medical report to an archiver for the ultrasound examination. In an example, a department head (e.g., director) can anonymize the benchmarking report (e.g., to remove the clinicians' names or other personal identifiers) and share the benchmarking report with the clinicians.

In embodiments, the benchmarking report includes comparisons of benchmarking data across entities, including comparisons across different care facilities (e.g., hospitals) and/or across departments within a care facility. For instance, a benchmarking report can compare benchmarking data for ultrasound examinations performed in an emergency department of a care facility to benchmarking data for ultrasound examinations performed in a critical care department of the care facility.

Additionally or alternatively, the benchmarking report can include comparisons of benchmarking data for ultrasound examinations performed using ultrasound equipment manufactured by different equipment manufacturers. Hence, the benchmarking report can compare the effectiveness of one equipment manufacturer to another equipment manufacturer, such as by comparing confidence values for parameters measured by ultrasound machines of the equipment manufacturers, e.g., confidence values for cardiac ejection fraction measured during ultrasound examinations performed with ultrasound machines of different manufacturers. In an example, the benchmarking report compares numbers and/or types of ultrasound examinations performed with ultrasound machines of different manufacturers. In an example, the benchmarking report compares ultrasound data in medical reports for ultrasound examinations performed with ultrasound machines of different manufacturers, such as inferences generated by machine-learned models implemented on ultrasound machines of different manufacturers.

In aspects, a benchmarking report can be customized by a user (e.g., a clinician, department head, director, etc.). For instance, a user can customize a benchmarking report by generating a configuration file that determines what information is to be included in the benchmarking report and how the information is to be presented in the benchmarking report. For example, the customization can control what clinicians are compared in the benchmarking report, and time intervals for medical reports submissions by the clinicians. Hence, a user can select a list of clinicians, and a time interval of one day or greater, to instruct the benchmarking report to include those clinicians on the list that submitted medical reports for ultrasound examinations later than 24 hours from the completion of the ultrasound examinations. A user may customize a benchmarking report via an ultrasound benchmarking software application accessible to the user. A dashboard can be displayed as part of the ultrasound benchmarking software application, and a user can input data for customizations via the dashboard.

In an example, a user can customize a frequency that benchmarking reports are delivered to the user (e.g., weekly, monthly, quarterly, etc.). Additionally or alternatively, a user can customize a delivery method by which a benchmarking report is delivered to the user (e.g., via email, or granting access through an application on a computing device, such as an ultrasound benchmarking software application that is installed on a tablet or smart phone operated by the user).

In one example, a user can customize the presentation of a benchmarking report, including an order that information is presented within the benchmarking report and/or a presentation format for the data in the benchmarking report. For instance, a first user may customize a benchmarking report so that data comparing clinicians is presented before data comparing departments within a care facility, and select a graph style so that graphs of the data include bar graphs. However, a second user may customize a benchmarking report so that data comparing clinicians is presented after data comparing the departments within a care facility, and select a graph style so that graphs of the data include pie charts. In embodiments, the customization can include a file format for an output file of a benchmarking report. For example, a user may export data from a benchmarking report to a file, and designate the file format, such as a "csv" format (a text file with comma separated values), an ascii text file, a pdf file, etc.

In embodiments, the system can generate a benchmarking report that can be used for education and training, such as to compare the performance of sonography students as part of the sonography credentialing. Hence, an instructor can customize a benchmarking report to display benchmarking data for students under the tutelage of the instructor. In an example, the instructor can anonymize the benchmarking report (e.g., to remove the students' names or other personal identifiers) and share the benchmarking report with the students.

In embodiments, a user (e.g., a department head or director) may customize a number and type of benchmarking reports that are generated. For instance, the user may configure a first benchmarking report for cardiac-focused examinations, a second benchmarking report for lung-focused examinations, and a third benchmarking report to compare students training to be credentialed sonographers.

Figure 2:
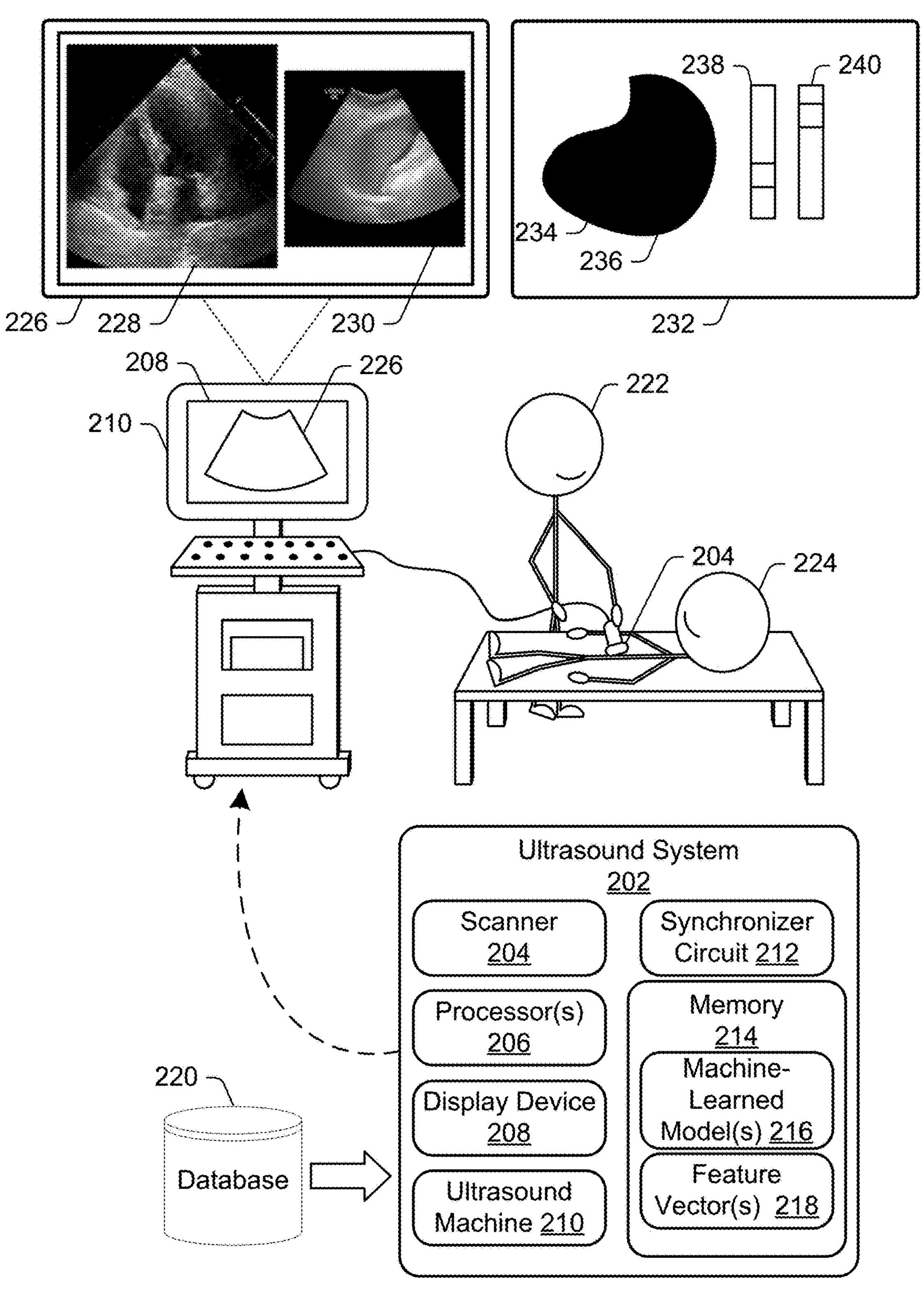
FIG. 2 illustrates an environment with an ultrasound system for contextual processing of ultrasound data in accordance with some embodiments.

FIG. 2 illustrates generally at environment 200 an ultrasound system 202 for contextual processing of ultrasound data in accordance with some embodiments. The ultrasound system 202 includes an ultrasound scanner 204 (which can also be referred to as an ultrasound transducer or ultrasound probe). The ultrasound system 202 also includes one or more processors (e.g., processor systems) 206. The processor 206 can include any suitable processor and number of processors, such as one or more CPUs, GPUs, vector processors, RISC processors, CISC processors, VLIW processors, etc. The processor 206 can execute instructions stored on a memory 214 to perform operations disclosed herein for contextual processing of ultrasound data. The ultrasound system 202 also includes a display device 208 that can include any suitable number and type of display devices, including a clinical display, tablet, smart phone, smart watch, goggles, glasses, television, flat panel, touch screen, holographic display, combinations thereof, and the like. The ultrasound system 202 also includes an ultrasound machine 210, such as a point-of-care ultrasound machine.

The ultrasound system 202 also includes a synchronizer circuit 212 that can be implemented to synchronize video clips with one another. For example, the ultrasound system 202 can obtain video clips that can be generated in different ways and/or stored in different formats. For instance, one video clip can be generated so that it includes an integer number of cycles of a waveform (e.g., an ECG waveform or M-mode ultrasound image), and another video clip can be generated so that it includes a designated time duration of the waveform, and can thus include a fractional, rather than integer, number of cycles of the waveform. The synchronizer circuit 212 can synchronize the two waveforms so that when the display device 208 displays the two video clips simultaneously (e.g., side-by-side), they are also synchronously displayed in the sense that they start at the same time point with respect to a cycle of the waveform. In some embodiments, the synchronizer circuit 212 synchronizes two video clips of ultrasound data that are obtained on different ultrasound machines manufactured by different ultrasound equipment manufacturers. The synchronizer circuit 212 can include any suitable circuitry to synchronize two or more video clips and/or waveforms, such as a phase locked loop, direct digital synthesizer, clock tree, correlator, etc.

The ultrasound system 202 also includes memory 214, which can include any suitable memory storage device. The memory 214 stores instructions to implement one or more machine-learned models 216, which can include one or more neural networks. The neural networks 104 and 106 of FIG. 1 are examples of the machine-learned models 216. The memory 214 also stores feature vectors as previously described. A database 220 is coupled to the ultrasound system 202, and the database 220 can store and provide contextual data that the ultrasound system can populate into the feature vectors 218. For instance, the database 220 can store data from ultrasound examinations, regional contextual data, patient contextual data, clinician contextual data, examination contextual data, and any other suitable contextual data that the ultrasound system 202 can use to construct the feature vectors 218.

The environment 200 depicts a clinician 222 (e.g., a sonographer or ultrasound operator) performing an ultrasound examination on a patient 224 using a scanner 204 and an ultrasound machine 210. The display device 208 of the ultrasound machine 210 depicts display data 226. In the example illustrated, the display data 226 includes a first ultrasound image 228 and a second ultrasound image 230. The first ultrasound image 228 can be an ultrasound image from a previous ultrasound exam and be provided to the ultrasound system 202 by the database 220. The second ultrasound image 230 can be an ultrasound image generated by the ultrasound machine 210 for the ultrasound examination currently being performed in the environment 200. In some other embodiments, the first ultrasound image 228 and the second ultrasound image 230 can be ultrasound images from previous ultrasound examinations.

The first ultrasound image 228 and the second ultrasound image 230 are examples of display data 226 that can be displayed by the ultrasound system 202 during an ultrasound examination. Other examples of the display data 226 include a patient recommendation, confidence value, audit report, grade/score, trend of measured parameters, email, and/or other output 108 as previously described with respect to FIG. 1. In some embodiments, the ultrasound system 202 generates a composite image by combining previous and current ultrasound data. For example, display data 232 illustrates another example of the display data 226. In the display data 232, the ultrasound system 202 overlays a segmentation 234 of a patient anatomy from a previous ultrasound image (e.g., an image generated from a previous ultrasound examination) with a segmentation 236 of the patient anatomy from a current ultrasound image (e.g., an image generated from a current ultrasound examination). The overlay can easily visualize the change in the patient anatomy between the ultrasound examinations. A user can adjust the opacity of one or both segmentations to help visualize the change, e.g., by using a slider control 238 for opacity adjustment of the segmentation 234 and a slider control 240 for opacity adjustment of the segmentation 236.

Additionally or alternatively, the ultrasound system 202 can generate a composite three-dimensional (3D) image by combining previous and current ultrasound data. For example, the ultrasound system 202 can include a machine-learned model to select views in ultrasound images from different ultrasound examinations to construct a 3D representation of a patient anatomy. The patient anatomy may not be expected to change shape over the duration of the ultrasound examinations, such as a bone. By using views from multiple ultrasound examinations, the ultrasound system 202 can construct a better 3D representation compared to using views from a single ultrasound examination. This can be particularly advantageous when some views are corrupted or obstructed for one ultrasound examination, such as because of equipment malfunction, clinician error, patient movement, a patient-worn device (e.g., a cast), etc.

Additionally or alternatively, the ultrasound system 202 can generate a video clip by combining previous and current ultrasound data. For example, the ultrasound system 202 can generate a video clip to illustrate the healing of an injury over time, by combining ultrasound images from multiple ultrasound examinations, and play the video clip on the display device 208 as part of the display data 226. In another example, the ultrasound system 202 can generate a video clip to illustrate the growth of a fetus over time, by combining ultrasound images from multiple ultrasound examinations, and play the video clip on the display device 208 as part of the display data 226. As described above, the ultrasound system can include one or more machine-learned models (e.g., neural networks) to select the image data from multiple ultrasound examinations and generate the video clip. In some embodiments, the machine-learned models can translate and rotate the image data so that it is stabilized when the video clip is played.

In some embodiments, the ultrasound system 202 synchronizes at least two video clips and/or waveforms using the synchronizer circuit 212 as previously described, and the display data 226 includes the simultaneous and synchronous display of the video clips/waveforms. Additionally or alternatively, the display data 226 can include any suitable graph of a measured parameter over time, such as ejection fraction, left ventricle size, etc. The graph can include data from multiple ultrasound examinations. Additionally or alternatively, the display data 226 can include a medical worksheet in which medical data, including ultrasound data, can be archived as part of a medical records archiver.

In some embodiments, for any data displayed as part of the display data 226, a user can select the data, such as by double tapping on the data value or a field name referring to the data value. Responsive to this user input, the ultrasound system 202 can retrieve and display the ultrasound image from which the selected data is derived. For example, if the display device 208 is displaying a medical worksheet that populates a data field with a value, such as a number for an ejection fraction, and the user selects the value, the ultrasound system 202 can automatically display the ultrasound image from which the ejection fraction is calculated. Depending on the parameter selected, its derivation in some cases can be traced back to multiple ultrasound images. In this case, the ultrasound system 202 can provide for the display of each of these images, such as in a matrix/grid display, a pull-down tab to select and display any one of the images, a video clip comprised of the images, or any suitable display format for the multiple ultrasound images.

In some embodiments, when an ultrasound image (or video clip) is saved, the ultrasound system 202 can automatically and without explicit user instruction execute one or more machine-learned models (e.g., neural networks) to process the ultrasound image (or video clip) and generate any suitable inferences. For instance, the ultrasound system 202 can automatically select a first neural network trained to detect pneumothorax and a second neural network trained to select free fluid and execute these two neural networks. The inferences generated by the neural networks can be compared to results determined manually by the clinician, thus serving as a quality check against the manually generated results.

In some embodiments, the ultrasound system 202 obtains contextual data that represents a context for the ultrasound examination and that is generated separately from the ultrasound examination. For instance, the contextual data can be obtained from the database 220. The contextual data can include ultrasound data generated by the clinician 222, but for a different patient than the patient 224. The contextual data can include a designator of the hospital/care facility, or any other suitable contextual data to provide a context for the ultrasound examination. Based on the contextual data, the ultrasound system 202 can select one or more neural networks from the machine-learned models 216. In some embodiments, when the contextual data indicates a particular care facility for the ultrasound examination, the ultrasound system 202 can select a neural network to generate an inference that the care facility may not be an expert in, such as for generating cardiac inferences. In some other embodiments, when the contextual data indicates a particular clinician, the ultrasound system 202 can select a neural network to generate an inference that the clinician is not an expert in, or has recently had poor grades in, etc. The ultrasound system 202 can then automatically execute the neural networks selected based on the contextual data to generate inferences for the ultrasound examination.

In some embodiments, the ultrasound system 202 can automatically populate a dashboard with the generated inferences. The dashboard can be viewable by a director or administrator of a department that manages ultrasound examinations, including the ultrasound examination illustrated in the environment 200. The ultrasound system 202 can also populate the dashboard with the contextual data, to provide a context for the inferences and their selection to the viewer of the dashboard.

FIG. 3 illustrates an example dashboard 300 for contextual processing of ultrasound data in accordance with some embodiments. The dashboard 300 can also be referred to as a user interface, and can be displayed to any suitable personnel, including a director or administrator of a department that manages ultrasound examinations. In some embodiments, the dashboard 300 is displayed by an ultrasound system, such as the ultrasound system 202 on the display device 208, so that the dashboard 300 can be viewed by a clinician operating the ultrasound system. The dashboard 300 includes an inference panel 302, a parameter trend panel 304, a worksheet panel 306, an audit report panel 308, a recommendation panel 310, an exam schedule panel 312, and an ultrasound image panel 314.

The inference panel 302 can display an inference generated by a machine-learned model, such as an inference generated by the neural network 104 in FIG. 1. In the example illustrated in FIG. 3, the inference panel 302 displays a segmentation of a left cardiac ventricle. The parameter trend panel 304 can display in any suitable format one or more measured values from one or more ultrasound examinations. In the example illustrated in FIG. 3, the parameter trend panel 304 displays a graph of a measured value, such as ejection fraction over time. The data points of the graph can be obtained from multiple ultrasound examinations for a patient. For instance, the seven data points shown in the graph in the parameter trend panel 304 can include six data points from six previous ultrasound examinations and one data point from a current ultrasound examination.

The worksheet panel 306 can display data from a medical worksheet, e.g., for a patient undergoing an ultrasound examination. In the example illustrated in FIG. 3, the worksheet panel 306 displays fields for ejection fraction and left ventricle size, and these fields are populated with data from the ultrasound examination. In an example, a user can select a value (or field populated with the value) displayed in the dashboard 300, and in response to the user selection, the dashboard 300 can display the ultrasound image, ultrasound images, or video clip from which the selected value is derived. In FIG. 3, a user selects the left ventricle size value in the worksheet panel 306, indicated by the fingerprint 316. For instance, the user can tap on the value of the left ventricle size, or the field name "left ventricle size". In response to the user selection indicated by the fingerprint 316, the dashboard 300 displays the ultrasound image panel 314. In some embodiments, prior to the user selection indicated by the fingerprint 316, the dashboard 300 did not display the ultrasound image panel 314. The ultrasound image panel 314 displays an ultrasound image from which the left ventricle size of 2.67 displayed in the worksheet panel 306 was determined (e.g., calculated).

The audit report panel 308 can display data included in an audit report, such as an audit report generated by the neural network 106 in FIG. 1 based on contextual processing of ultrasound data. In the example illustrated in FIG. 3, the audit report panel 308 displays a clinician grade of a "B−". This grade can be assigned by the neural network 106 for an ultrasound examination performed by the clinician. The audit report panel 308 also displays a confidence value of 0.87. This value can correspond to an inference generated by a neural network, such as the segmentation displayed in the inference panel 302. The audit report panel 308 also displays a prediction value of 0.79 for an ejection fraction parameter. This prediction value can be generated as an output 108 by the neural network 106 in FIG. 1 and represent an expected (or target, or desired) value of the ejection fraction for the patient when the ejection fraction is measured at the next ultrasound examination. The audit report panel 308 also displays a ranking of clinicians, such as sonographers in a department of a hospital. The ranking can be based on ultrasound examinations performed by the clinicians and the output 108 generated by the neural network 106 in FIG. 1 for the ultrasound examinations. In this example, the audit report ranks clinician "Davin" first, and clinician "Tom" last, with clinicians "David", "Chris", and "Kristine" in between.

The recommendation panel 310 can display data included in a recommendation, e.g., a patient recommendation, such as a recommendation generated as part of the output 108 by the neural network 106 in FIG. 1 and/or a recommendation generated by a clinician. In the example illustrated in FIG. 3, the recommendation panel 310 includes a recommendation for medication including 20 mg of Warfarin and a visit to a cardiologist named Dr. Smith on June 15 at 10:00 AM. The recommendation also includes a subsequent ultrasound examination scheduled for June 1 at 9:30 AM, and a diet recommendation to eat less red meat. The recommendation panel 310 also indicates that recommendation emails were sent to the patient and the clinician on May 8, 2023.

The exam schedule panel 312 can display any suitable scheduling data for ultrasound examinations that are scheduled or have already been performed. In the example illustrated in FIG. 3, the exam schedule panel 312 indicates that clinician "Davin" has an ultrasound examination scheduled for 2:00 PM today with patient "P. Pena" and another ultrasound examination scheduled for 3:00 PM today with patient "L. George". The exam schedule panel 312 also indicates that clinician "Kristine" performed two ultrasound examination today, one for patient "B. Weir" at 9:30 AM and one for patient "J. Garcia" at 10:30 AM.

Figure 4:
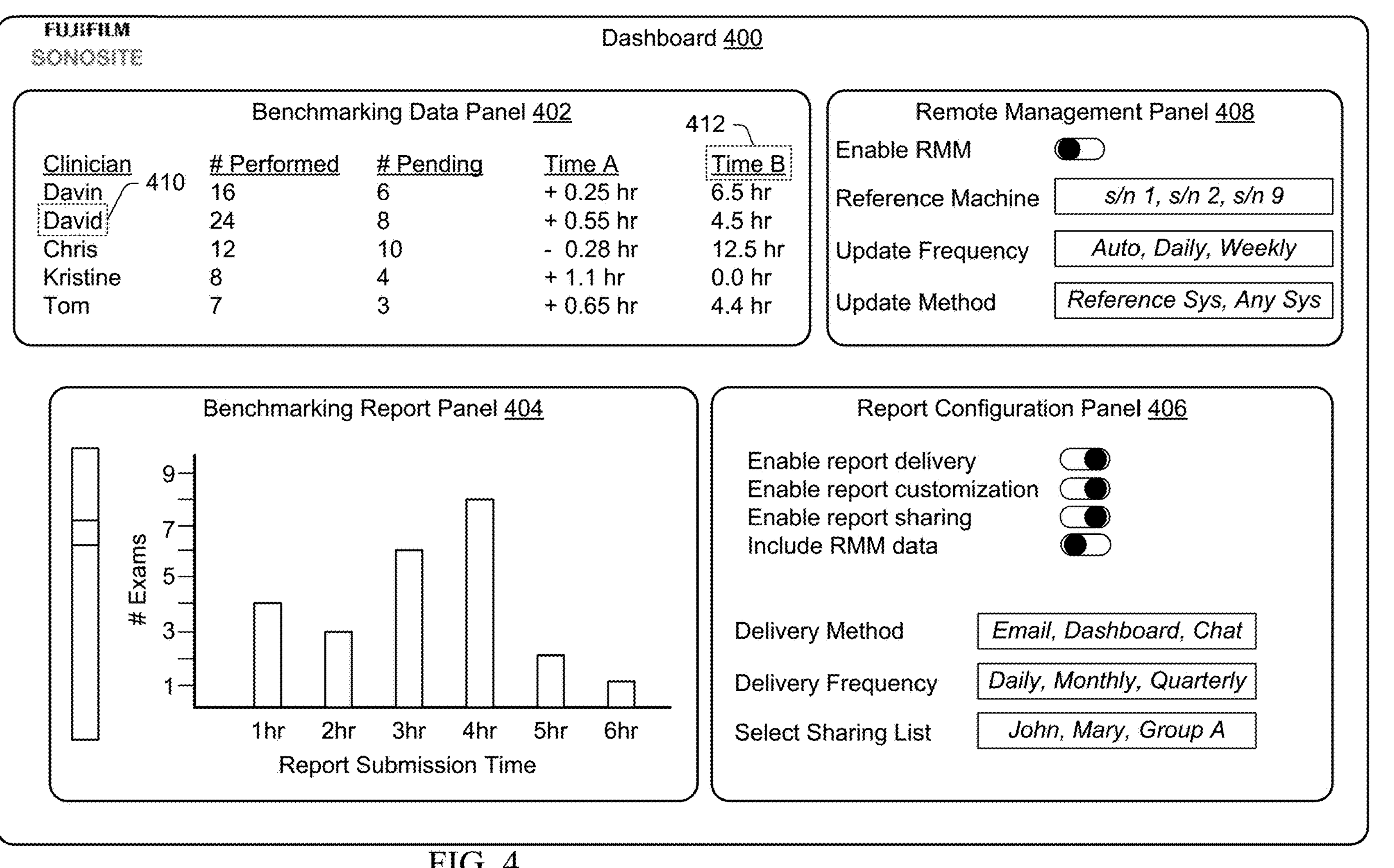
FIG. 4 illustrates an example dashboard that can be displayed by an ultrasound system in accordance with some embodiments.

FIG. 4 illustrates an example of a dashboard 400 that can be displayed by an ultrasound system in accordance with the present invention. The dashboard 400 includes a benchmarking data panel 402, a benchmarking report panel 404, a report configuration panel 406, and a remote management panel 408. The benchmarking data panel 402 can display any suitable benchmarking data, including ultrasound data generated as part of ultrasound examinations, contextual data representing a context for the ultrasound examinations, scheduling data representing schedules for the ultrasound examinations, and reporting data representing medical reports generated for the ultrasound examinations. In the example illustrated in FIG. 4, the benchmarking data panel 402 displays a list of clinicians (left-most column) and a table of benchmarking data for each clinician. The table includes a column for the number of ultrasound examinations performed by the clinicians (e.g., over a specified time interval, such as weekly, or since a user-selected time and date). The table also includes a column for the number of pending (e.g., scheduled) ultrasound examinations for each clinician. The table also includes a column labeled "Time A" that indicates an average timeliness for starting ultrasound examinations relative to scheduled times for each clinician. As an example in FIG. 4, clinician Davin starts ultrasound examinations an average of 0.25 hours late relative to the scheduled starting time. The table also includes a column labeled "Time B" that indicates an average timeliness for submitting medical reports relative to the finish time of ultrasound examinations. As an example in FIG. 4, clinician Davin submits medical reports for ultrasound examinations an average of 6.5 hours after the ultrasound examination is completed. The columns of data in the benchmarking data panel 402 are exemplary and non-limiting. Generally, a user can customize the dashboard 400 so that the benchmarking data panel 402 includes benchmarking data suitable for the user.

In the example of FIG. 4, a user has selected clinician David (indicated by the dashed box 410) and column "Time B" (indicated by the dashed box 412). Responsive to these user selections, the ultrasound system causes the dashboard 400 to display the benchmarking report panel 404, which displays for clinician David a histogram of report submission times. For instance, the benchmarking report panel 404 includes a histogram including the number of report submissions submitted from one hour to six hours after the completion of ultrasound examinations, in one-hour increments. When a user selects multiple clinicians from the benchmarking data panel 402, the benchmarking report panel 404 can display data comparing the benchmarking data across the selected clinicians, such as comparative histograms for the selected data in the column labeled "Time B".

The report configuration panel 406 can display any suitable data and user options for configuring a benchmarking report. In FIG. 4, the report configuration panel 406 includes binary selections to enable benchmarking report delivery to a user, to enable benchmarking report customization, to enable benchmarking report sharing, and to enable the inclusion of remote management and monitoring (RMM) data in the benchmarking report. The report configuration panel 406 also includes selections with pull-down tabs for selecting a delivery method for benchmarking reports (e.g., via email, dashboard display, or chat), a delivery frequency of the benchmarking reports (e.g., daily, monthly, quarterly), and for selecting a sharing list including individuals or groups of individuals to share a benchmarking report with. Although not shown for clarity, the report configuration panel 406 can also include selections for configuring the histogram displayed in the benchmarking report panel 404, such as the time intervals over which the histogram is calculated (e.g., one hour as shown vs. half-hour intervals for more granularity).

The remote management panel 408 can display any suitable data for configuring RMM. In the example in FIG. 4, the remote management panel 408 displays a binary selection to enable and disable RMM of ultrasound systems. The remote management panel 408 also includes selections with pull-down tabs for selecting one or more reference ultrasound machines for propagating changes to other ultrasound machines (e.g., by machine serial number or name), selecting an update frequency for changes/updates to ultrasound systems via RMM (e.g., automatically upon a change to a reference system, daily, weekly, etc.), and for selecting an update method (e.g., based on changes to a reference system only, or based on changes to any system).

Although not shown in FIG. 4 for clarity, the dashboard 400 can also include a telemedicine panel for enabling and controlling telemedicine, including crowd-sourced review of ultrasound data. Hence, a telemedicine panel can include lists of clinicians and their specialties, options to invite a clinician to review the ultrasound data, options to accept a request from a clinician for review of the ultrasound data, and the like.

An Example System

Figure 5:
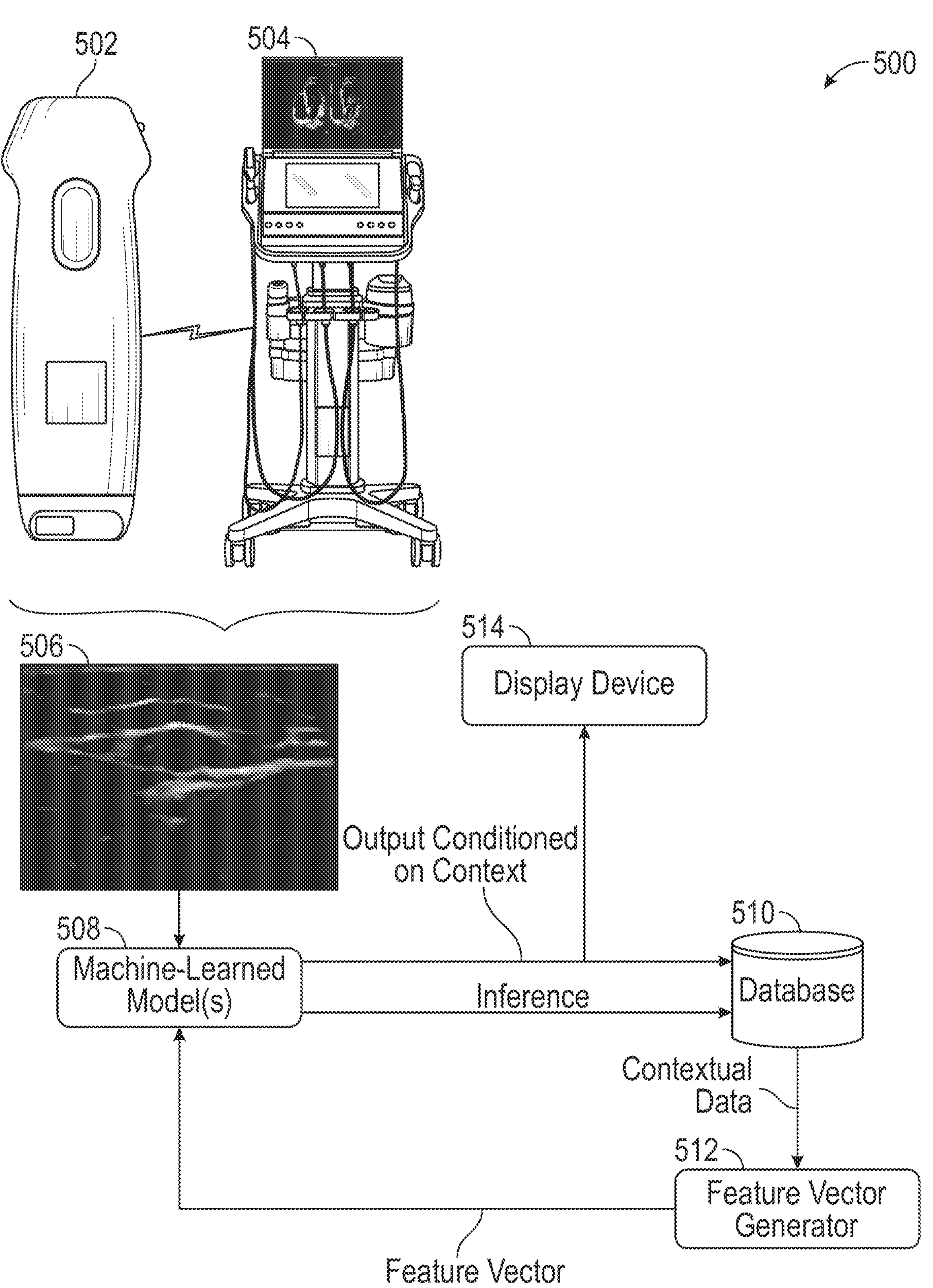
FIG. 5 illustrates an ultrasound system for contextual processing of ultrasound data in accordance with some embodiments.

FIG. 5 illustrates an ultrasound system 500 for contextual processing of ultrasound data in accordance with some embodiments. The ultrasound system 202 in FIG. 2 is an example of the ultrasound system 500.

The ultrasound system 500 includes an ultrasound scanner 502 coupled to an ultrasound machine 504. The ultrasound scanner 502 and the ultrasound machine 504 can be coupled wired, wirelessly, or a combination thereof, and can be used during an ultrasound examination to generate an ultrasound image 506. The ultrasound system 500 provides the ultrasound image 506 to machine-learned model(s) 508. The neural networks 104 and 106 in FIG. 1 and the machine-learned model(s) 216 in FIG. 2 are examples of the machine-learned model(s) 508. The machine-learned model(s) 508 generate an inference based on the ultrasound image 506, such as an object detection, object classification, object segmentation, probability, measurement, and the like. The machine-learned model(s) 508 provide the inference to the database 510 for storage.

The database 220 in FIG. 2 is an example of the database 510. The database 510 stores and/or has access to contextual data for an ultrasound examination, such as regional features, patient features, clinician features, examination features, and the like, as previously described. In some embodiments, the database 510 is connected to a network (not shown in FIG. 5) and can receive at least some of the contextual data over the network from a source outside the care facility that operates the ultrasound system 500. For instance, the source can include a weather station that provides weather data to the care facility. The database 510 provides the contextual data to a feature vector generator 512.

The feature vector generator 512 can be implemented in a processor of the ultrasound system 500, such as the processor 206 previously described with respect to FIG. 2. The feature vector generator 512 populates a feature vector with the contextual data or data derived from the contextual data and provides the feature vector to the machine-learned model(s) 508. The machine-learned model(s) 508 execute at least one machine-learned model, such as a neural network, that processes the ultrasound image 506 and at least one additional input that includes the feature vector to generate output conditioned on context. In an example, the at least one additional input includes the feature vector and the inference. The output conditioned on context can include a patient recommendation, audit report, grade, score, email, trend of measured parameters, prediction for a measured parameter, and the like, as previously described. The output 108 in FIG. 1 is an example of the output conditioned on context. The machine-learned model(s) 508 provide the output conditioned on context to the database 510 so that it can be used as contextual data for a subsequent ultrasound examination, and also to a display device 514 for user consumption. The display device 514 can display a dashboard, such as the dashboard 300 in FIG. 3, that displays the output conditioned on context. In one example, the ultrasound machine 504 includes the display device 514.

In some embodiments, the ultrasound system 500 selects at least one machine-learned model, e.g., a neural network, to process the ultrasound image 506 based on the contextual data in the feature vector. For instance, the ultrasound system 500 can select a neural network to generate cardiac inferences if the contextual data indicates a care facility or clinician having low grades for cardiac imaging results. The ultrasound system 500 can automatically and without user intervention execute the selected machine-learned model(s)

and populate the dashboard with results (e.g., inferences) generated by the selected machine-learned model(s).

An Example Machine-Learned Model

Many of the aspects described herein can be implemented using a machine-learned model. For the purposes of this disclosure, a machine-learned model is any model that accepts an input, analyzes and/or processes the input based on an algorithm derived via machine-learning training, and provides an output. A machine-learned model can be conceptualized as a mathematical function of the following form:

$$f(\hat{s}, \theta) = \hat{y} \quad \text{Equation (1)}$$

In Equation (1), the operator f represents the processing of the machine-learned model based on an input and providing an output. The term s represents a model input, such as ultrasound data. The model analyzes/processes the input s using parameters θ to generate output ŷ (e.g., object identification, object segmentation, object classification, etc.). Both ŝ and ý can be scalar values, matrices, vectors, or mathematical representations of phenomena such as categories, classifications, image characteristics, the images themselves, text, labels, or the like. The parameters θ can be any suitable mathematical operations, including but not limited to applications of weights and biases, filter coefficients, summations or other aggregations of data inputs, distribution parameters such as mean and variance in a Gaussian distribution, linear algebra-based operators, or other parameters, including combinations of different parameters, suitable to map data to a desired output.

Figure 6:
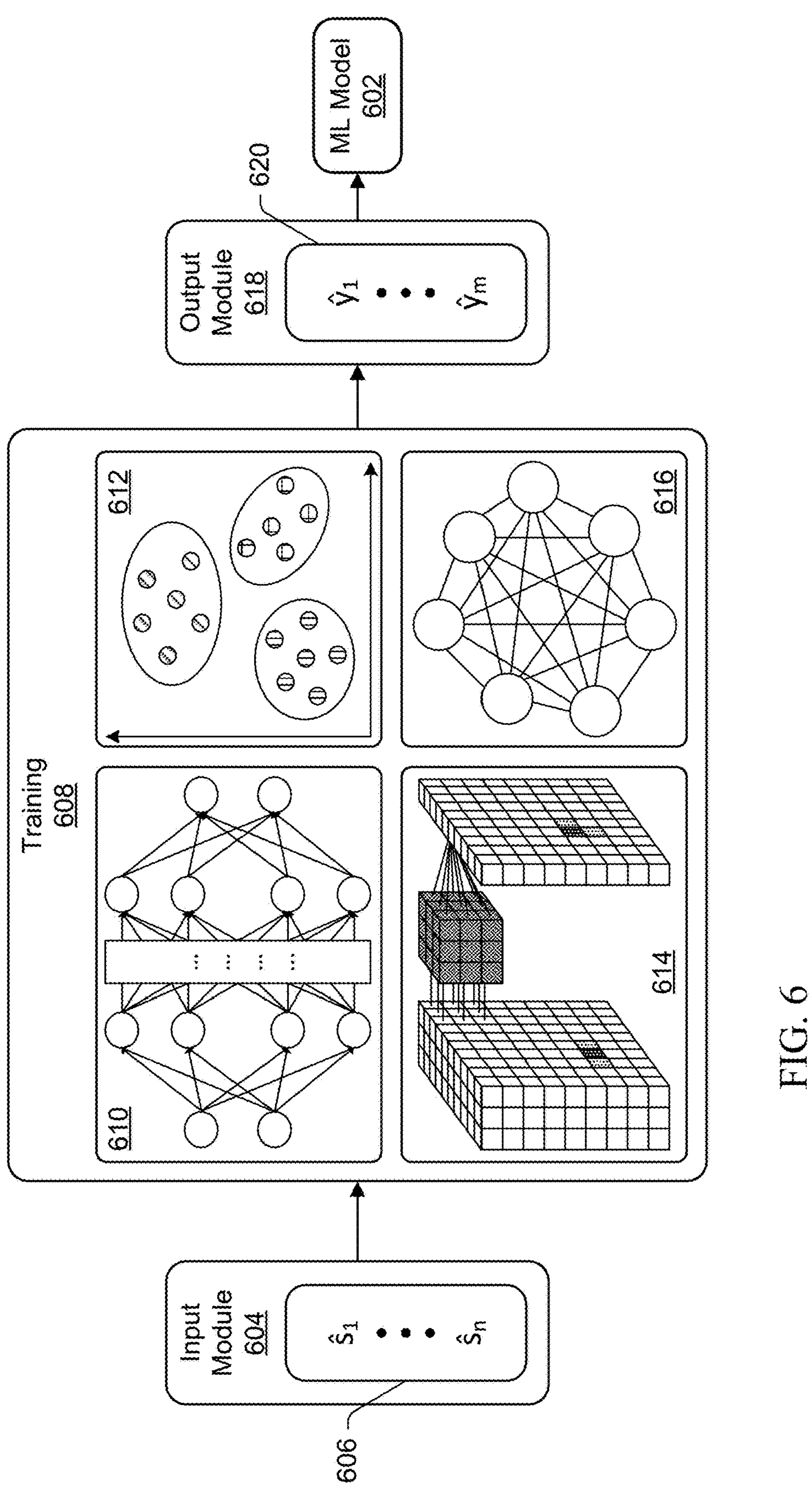
FIG. 6 represents an example machine-learning architecture used to train a machine-learned model in accordance with some embodiments.

FIG. 6 represents an example machine-learning architecture 600 used to train a machine-learned model M 602 (e.g., machine-learned models 508 and 216) in accordance with some embodiments. An input module 604 accepts an input § 606, which can be an array with members $\hat{s}_1$ through $\hat{s}_n$. The input ŝ 606 is fed into a training module 608, which processes the input ŝ 606 based on the machine-learning architecture 600. For example, if the machine-learning architecture 600 uses a multilayer perceptron (MLP) model 610, the training module 608 applies weights and biases to the input ŝ 606 through one or more layers of perceptrons, each perceptron performing a fit using its own weights and biases according to its given functional form. MLP weights and biases can be adjusted so that they are optimized against a least mean square, logcosh, or other optimization function (e.g., loss function) known in the art. Although an MLP model 610 is described here as an example, any suitable machine-learning technique can be employed, some examples of which include but are not limited to k-means clustering 612, convolutional neural networks (CNN) 614, a Boltzmann machine 616, Gaussian mixture models (GMM), and long short-term memory (LSTM). The training module 608 provides an input to an output module 618. The output module 618 analyzes the input from the training module 608 and provides an output in the form of ŷ 620, which can be an array with members $\hat{y}_1$ through $\hat{y}_m$. The output ŷ 620 can represent a known correlation with the input ŝ 606, such as, for example, object identification, segmentation, and/or classification.

In some embodiments, the input ŝ 606 can be a training input labeled with known output correlation values, and these known values can be used to optimize the output ŷ 620 in training against the optimization/loss function. In other examples, the machine-learning architecture 600 can categorize the output ŷ 620 values without being given known correlation values to the inputs ŝ 606. In some embodiments, the machine-learning architecture 600 can be a combination of machine-learning architectures. By way of example, a first network can use the input ŝ 606 and provide the output ŷ 620 as an input SML to a second machine-learned architecture, with the second machine-learned architecture providing a final output $\hat{y}_f$. In some other embodiments, one or more machine-learning architectures can be implemented at various points throughout the training module 608.

In some machine-learned models, all layers of the model are fully connected. For example, all perceptrons in an MLP model act on every member of s. For an MLP model with a 100×100 pixel image as the input, each perceptron provides weights/biases for 10,000 inputs. With a large, densely layered model, this may result in slower processing and/or issues with vanishing and/or exploding gradients. A CNN, which may not be a fully connected model, can process the same image using 5×5 tiled regions, requiring only 25 perceptrons with shared weights, giving much greater efficiency than the fully connected MLP model.

Figure 7:
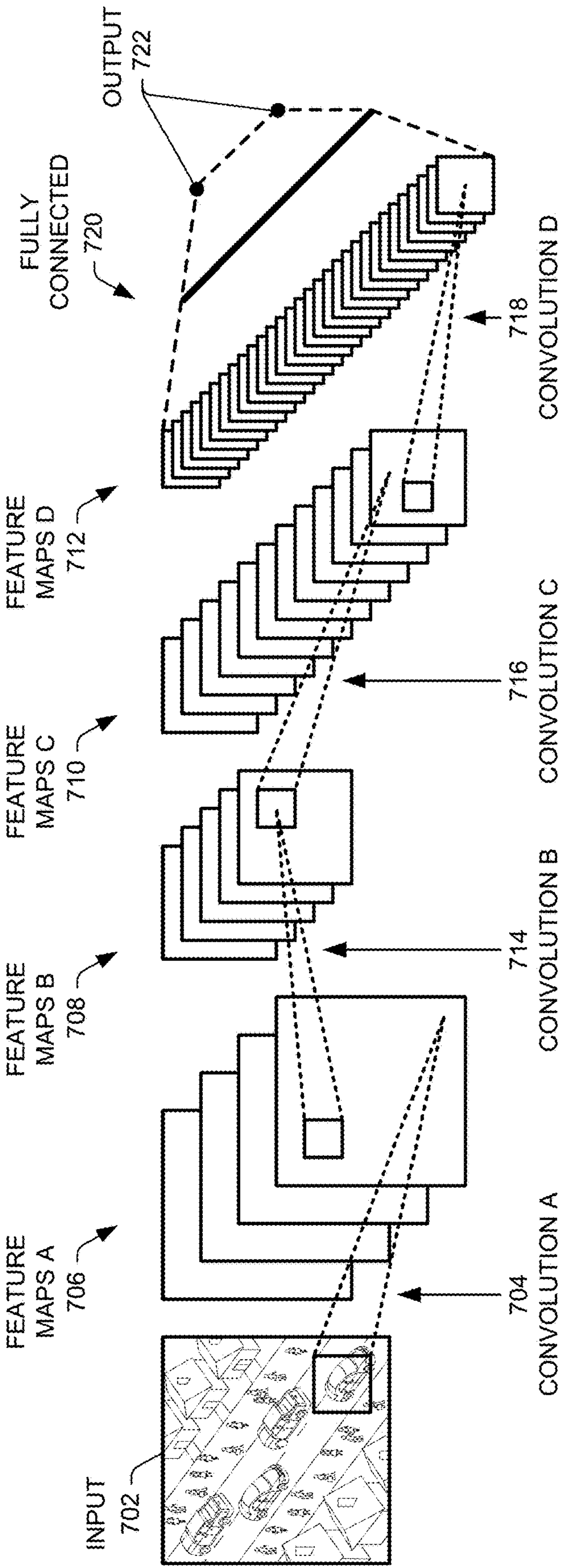
FIG. 7 represents an example machine-learned model using a CNN to process an input image in accordance with some embodiments.

FIG. 7 represents an example machine-learned model 700 using a CNN to process an input image 702 in accordance with some embodiments. In some embodiments, the input image 702 includes representations of objects that can be identified via object recognition, such as people or cars (or an anatomy, as described in relation to FIGS. 1-4). Convolution A 704 can be performed to create a first set of feature maps (e.g., feature maps A 706). A feature map can be a mapping of aspects of the input image 702 given by a filter element of the CNN. This process can be repeated using feature maps A 706 to generate further feature maps B 708, feature maps C 710, and feature maps D 712 using convolution B 714, convolution C 716, and convolution D 718, respectively. In this example, the feature maps D 712 become an input for fully connected network layers 720. In this way, the machine-learned model can be trained to recognize certain elements of the image, such as people, cars, or a particular patient anatomy, and provide an output 722 that, for example, identifies the recognized elements. In some embodiments, the feature vector and/or inference generated with the ultrasound system 500 can be appended to a feature map (e.g., feature map B 708) generated by a neural network (e.g., CNN). In this way, the feature vector and/or inference can be used as a secondary/conditional input to the neural network.

Although the example of FIG. 7 shows a CNN as a part of a fully connected network, other architectures can be used and this example should not be seen as limiting. There can be more or fewer layers in the CNN. A CNN component for a model can be placed in a different order, or the model can contain additional components or models. There may be no fully connected components, such as a fully convolutional network. Additional aspects of the CNN, such as pooling, downsampling, upsampling, or other aspects known to people skilled in the art can also be employed.

Example Procedures

FIG. 8 illustrates an example method 800 that can be implemented by an ultrasound system in accordance with some embodiments. The ultrasound system can include an ultrasound scanner, an ultrasound machine, a processor system, a display device, and a synchronizer circuit. In some embodiments, the ultrasound system includes a wearable component, such as a patch with a transducer array. Operations of the method are performed by processing logic that can comprise hardware (circuitry, dedicated logic, etc.), software (such as is run on a general-purpose computer system or a dedicated machine), firmware, or combinations thereof.

In some embodiments, ultrasound is transmitted at a patient anatomy and ultrasound data is generated as part of an ultrasound examination (block 802). For example, an ultrasound scanner can transmit ultrasound at a patient anatomy and generate ultrasound data as part of the ultrasound examination. An ultrasound image is generated based on the ultrasound data (block 804). For example, an ultrasound machine can generate, based on the ultrasound data, the ultrasound image. Features are selected from the group consisting of regional features, patient features, clinician features, and ultrasound examination features (block 806). For example, a processor system can select the features. A patient recommendation is generated based on the ultrasound image and the features (block 808). For example, the processor system can generate the patient recommendation.

In an example, the features include the regional features, and the regional features include at least one of a population size, a population density, a pollution level, a number of airports, a zip code, and a regional news event. Additionally or alternatively, the features can include the patient features, and the patient features include at least one of a patient age, a patient weight, a symptom description, patient genomic data, and a patient medical history. Additionally or alternatively, the features can include the clinician features, and the clinician features include at least one of a clinician age, an education level, a number of ultrasound examinations performed, and an amount of time since a vacation. Additionally or alternatively, the features can include the ultrasound examination features, and the ultrasound examination features include at least one of cleaning data for the ultrasound system, calibration data for the ultrasound system, radio frequency measurements obtained during the ultrasound examination, indicators of equipment proximate to the ultrasound system during the ultrasound examination, weather during the ultrasound examination, a time of day of the ultrasound examination, and a day of week of the ultrasound examination. In some embodiments, at least one of the features is unavailable during the ultrasound examination. For instance, the processor system can generate the patient recommendation after the ultrasound examination, using features that were not yet generated at the time of the ultrasound examination. For example, the features can include data from an additional ultrasound examination that was performed after the ultrasound examination.

In some embodiments, the processor system implements a neural network to generate, based on the ultrasound image, an inference for the patient anatomy. The processor system can implement an additional neural network to generate the patient recommendation based on the inference.

In some embodiments, the processor system is implemented to generate, based on the ultrasound image and the features, an audit report that compares the ultrasound examination and an additional ultrasound examination. The additional ultrasound examination can be performed by the same clinician who performed the ultrasound examination, or a different clinician.

In some embodiments, the patient recommendation includes at least one of an additional examination, a clinical trial, and a medication. The processor system can communicate the patient recommendation to the patient via an email. Additionally or alternatively, the patient recommendation can be displayed on a dashboard (e.g., user interface) viewable by a clinician and/or an administrator responsible for overseeing ultrasound examinations in a care facility.

In some embodiments, the ultrasound system includes a display device, and the processor system is implemented to obtain an additional ultrasound image generated during an additional ultrasound examination. The display device is implemented to simultaneously display the ultrasound image and the additional ultrasound image. For example, the ultrasound image and the additional ultrasound image can be displayed side-by-side. Additionally or alternatively, the ultrasound image and the additional ultrasound image can be part of video clips that are simultaneously played and exposed on the display device. The display device can be included in the ultrasound system, such as a clinical display or a tablet coupled to the clinical display.

In some embodiments, the ultrasound system includes a display device and a synchronizer circuit. The ultrasound machine is implemented to generate a video clip that includes the ultrasound image, and the processor system is implemented to obtain an additional video clip of ultrasound images. The synchronizer circuit can be implemented to synchronize the video clip and the additional video clip, and the display device can simultaneously and synchronously display the video clip and the additional video clip.

In some embodiments, the processor system can obtain an additional ultrasound image generated during a previous ultrasound examination and generate a first segmentation of the patient anatomy from the ultrasound image and a second segmentation of the patient anatomy from the additional ultrasound image. The display device can display the first segmentation and the second segmentation. For instance, display device can display the segmentations in side-by-side display. Additionally or alternatively, the display device can overlay the segmentations. The user can adjust the opacity/occlusion of one or both segmentations to show the margin/difference between the segmentations.

In some embodiments, the display device is implemented to display a user interface configured to display a value measured from the patient anatomy in the ultrasound image, such as an ejection fraction. The user interface can receive a user selection of the value. For instance, a user can touch the value on a touchscreen of the display device. Responsive to the user selection, the user interface can then display the ultrasound image.

FIG. 9 illustrates an example method 900 that can be implemented by an ultrasound system in accordance with some embodiments. The ultrasound system can include an ultrasound scanner, an ultrasound machine, a processor system, and a display device. Operations of the method are performed by processing logic that can comprise hardware (circuitry, dedicated logic, etc.), software (such as is run on a general-purpose computer system or a dedicated machine), firmware, or combinations thereof.

In some embodiments, ultrasound is transmitted at a patient anatomy and ultrasound data is generated as part of an ultrasound examination (block 902). For example, an ultrasound scanner can transmit ultrasound at a patient anatomy and generate ultrasound data as part of the ultrasound examination. An ultrasound image is generated based on the ultrasound data (block 904). For example, an ultrasound machine can generate, based on the ultrasound data, the ultrasound image. Contextual data that represents a context for the ultrasound examination and that is generated separately from the ultrasound examination is obtained (block 906). For example, the processor system can obtain the contextual data. Based on the ultrasound image and the contextual data, a confidence value for the ultrasound examination is generated (block 908). For example, the processor system can generate the confidence value.

In some embodiments, the processor system is implemented to populate a dashboard with the confidence value. The dashboard (or user interface) can be viewable by a director (e.g., administrator) of a department that manages ultrasound examinations including the ultrasound examination. The processor system can populate the dashboard with the contextual data.

In some embodiments, the contextual data includes regional data for a location where the ultrasound examination is performed. Additionally or alternatively, the contextual data can include clinician data for a clinician who performs the ultrasound examination. Additionally or alternatively, the contextual data can include examination data from an additional ultrasound examination performed by a clinician who performs the ultrasound examination.

FIG. 10 illustrates an example method 1000 that can be implemented by an ultrasound system in accordance with some embodiments. The ultrasound system can include an ultrasound scanner, an ultrasound machine, a processor system, a computer-readable memory device, and a display device. Operations of the method are performed by processing logic that can comprise hardware (circuitry, dedicated logic, etc.), software (such as is run on a general-purpose computer system or a dedicated machine), firmware, or combinations thereof.

In some embodiments, an ultrasound image is generated based on ultrasound data generated as part of an ultrasound examination (block 1002). For example, an ultrasound scanner can generate the ultrasound data and an ultrasound machine can generate the ultrasound image. Contextual data that represents a context for the ultrasound examination and that is generated separately from the ultrasound examination is obtained (block 1004). For example, the processor system can obtain the contextual data. Based on the contextual data, a neural network is selected (block 1006). For example, the processor system can select the neural network. Responsive to the ultrasound image being stored on the computer-readable memory device, one or more neural networks including the neural network are executed, the one or more neural networks configured to generate inferences for the ultrasound examination (block 1008). The processor system can execute the one or more neural networks. The inferences and/or the contextual data can be populated in a dashboard, as previously described. In an example, the contextual data represents the hospital and/or department where the ultrasound examination is performed. Additionally or alternatively, the contextual data can represent the clinician performing the ultrasound examination.

FIG. 11 illustrates an example method 1100 that can be implemented by an ultrasound system in accordance with some embodiments. The ultrasound system can include an ultrasound scanner, an ultrasound machine, a processor system, a display device, and a synchronizer circuit. In some embodiments, the ultrasound system includes a wearable component, such as a patch with a transducer array. Operations of the method are performed by processing logic that can comprise hardware (circuitry, dedicated logic, etc.), software (such as is run on a general-purpose computer system or a dedicated machine), firmware, or combinations thereof.

Benchmarking data for ultrasound examinations is maintained (block 1102). For instance, an archiver can maintain (including to store) the benchmarking data. The benchmarking data can include one or more of ultrasound data generated as part of the ultrasound examinations, contextual data representing a context for the ultrasound examinations, scheduling data representing schedules for the ultrasound examinations, and reporting data representing medical reports generated for the ultrasound examinations. A benchmarking report is generated that includes a comparison of the benchmarking data across the ultrasound examinations (block 1104). For example, a computing device coupled to the archiver and that implements an ultrasound benchmarking software application to display a dashboard can generate the benchmarking report. The benchmarking report including the comparison is displayed (block 1106). For example, a display device (e.g., user device) coupled to the computing device can display the benchmarking report. In an example, the computing device includes the display device.

In embodiments, at least one of the computing device and the display device is implemented to receive a user input indicating a selection of the benchmarking data to include in the comparison included in the benchmarking report. In an example, the benchmarking data includes ultrasound data obtained from at least two ultrasound equipment manufacturers, and the benchmarking report includes a visual representation that compares the ultrasound data obtained from the at least two ultrasound equipment manufacturers. For instance, the visual representation can include a graph in a style that is set (e.g., customized) by a user, and the ultrasound data can include measurements made on ultrasound machines manufactured from two or more equipment manufacturers. The user can customize the benchmarking report including to select the two or more equipment manufacturers from a list of ultrasound equipment manufacturers.

In embodiments, the benchmarking data includes reporting data for medical reports generated by at least two clinicians who performed the ultrasound examinations, and the benchmarking report compares submission timeliness for the medical reports generated by the at least two clinicians. For example, the benchmarking report can indicate the submission timeliness in a histogram for each clinician that shows the number of medical reports submitted for each hour subsequent to the completion of an ultrasound examination over a 24 hour period. As an example, for a given clinician, the first hour can indicate ten medical reports, the second hour can indicate five medical reports, and the third hour can indicate one medical report, for a total of 16 reports. In this example, the clinician completed most of their medical report submissions in the first hour after an ultrasound examination, and all of their medical report submissions within three hours after an ultrasound examination.

Additionally or alternatively, the benchmarking data can include scheduling data that indicates scheduled times for when the ultrasound examinations were scheduled to occur and actual times for when the ultrasound examinations did occur. The comparison can indicate differences between the scheduled times and the actual times.

In embodiments, an archiver is implemented to obtain the benchmarking data from at least two departments within a care facility, and the benchmarking report compares the at least two departments based on the benchmarking data. For instance, the benchmarking data can include scheduling data that indicates numbers of the ultrasound examinations performed within the at least two departments, and the comparison can indicate the numbers of the ultrasound examinations. Additionally or alternatively, the benchmarking data can include scheduling data that indicates types of the ultrasound examinations performed within the at least two departments, and the comparison can indicate the types of the ultrasound examinations. For example, the at least two departments can include an emergency department and an urgent care department within a care facility, and the benchmarking report can compare numbers of ultrasound examinations, types of ultrasound examinations, times of day for the ultrasound examinations, timeliness of medical report submissions for the ultrasound examinations, and the like, across the emergency department and the urgent care department.

Additionally or alternatively, the archiver can obtain the benchmarking data from at least two care facilities (e.g., two different hospitals). The benchmarking report can compare the at least two care facilities based on the benchmarking data.

In embodiments, at least one of the computing device and the display device is implemented to receive a user input indicating report times, and the display device is implemented to obtain and display the benchmarking report according to the report times. For instance, a user can customize the benchmarking report via a dashboard displayed on the computing device and/or the display device to indicate report times including a distribution frequency for which benchmarking reports are to be communicated by the system to the user, such as weekly, monthly, quarterly, etc. The system can communicate the benchmarking report to the user and cause the display of the benchmarking report on the display device in accordance with the user-selected distribution frequency.

In embodiments, at least one of the computing device and the display device is implemented to receive a user input indicating a delivery method of the benchmarking report to the display device. The delivery method can include at least one of email delivery and access via a benchmarking application configured to display a dashboard. In embodiments, the dashboard includes an option to invite a clinician to review the ultrasound data. Additionally or alternatively, the dashboard can include an option to accept a request from a clinician for review of the ultrasound data. Hence, the system can enable a crowd-sourced type of review of the ultrasound data from clinicians who may be local or remote with respect to the ultrasound examination.

In embodiments, the dashboard includes an option of remote monitoring and management of one or more ultrasound machines and/or systems used in one or more of the ultrasound examinations. For example, a user can enable, via the dashboard, the remote monitoring and management of one or more ultrasound machines/systems. In an example, the user can specify a group of ultrasound machines, and that if a change is made to one of the ultrasound machines in the group, the change is automatically propagated to the other ultrasound machines in the group. For instance, if a user defines a custom examination or protocol on a first ultrasound machine, the system automatically configures the other ultrasound machines with access to the custom examination or protocol so that the custom examination or protocol can be executed on the other ultrasound machines.

In an example, the user can designate one or more ultrasound machines as reference ultrasound machines, so that only changes made on a reference ultrasound machine are automatically propagated to other ultrasound machines. Additionally or alternatively, a user can configure a reference ultrasound machine to determine (e.g., via a network in a care facility) configuration changes made to other ultrasound machines, and then pull those changes into the reference ultrasound machine. The reference ultrasound machine can then push the changes out to other ultrasound machines that do not include the change. Additionally or alternatively, the care facility can include a smart network that normalizes all systems to a same configuration when any changes are made. Hence, the updates can occur in real time, e.g., responsive to changes made on an ultrasound machine. Alternatively, the updates can occur in batches, such as on a time basis (e.g., daily), on a quantity basis (e.g., once a user-defined number of changes have been made), or on a type basis (e.g., once a certain type of change is made, such as the creation of a new protocol). In examples, a reference ultrasound machine includes or has access to not only data for patient examinations performed using the reference ultrasound machine, but also data for patient examinations performed using other ultrasound machines. Another (non-reference) ultrasound machine, however, may include or have access to only patient examinations performed using this other ultrasound machine. Hence, using one or more of these remote management features, an administrator can easily keep a fleet of ultrasound machines up to date with current changes for the department managed by the administrator.

In embodiments, a user (e.g., an administrator) can view data related to the remote management and monitoring of ultrasound machines via a benchmarking report. For example, the benchmarking report can compare configuration data across ultrasound machines, including software updates, sources of software updates (e.g., reference ultrasound machines), added protocols, newly created examination presets, and the like. Additionally or alternatively, the benchmarking report can compare usage data across the ultrasound machines (e.g., ultrasound machines used for different types of ultrasound examinations), and compare the usage data to the configuration data. Hence, a user can determine from the benchmarking report the propagation of configuration updates to types of ultrasound examinations performed.

FIG. 12 illustrates an example method 1200 that can be implemented by an ultrasound system in accordance with some embodiments. The ultrasound system can include an ultrasound scanner, an ultrasound machine, a processor system, a display device, and a synchronizer circuit. In some embodiments, the ultrasound system includes a wearable component, such as a patch with a transducer array. Operations of the method are performed by processing logic that can comprise hardware (circuitry, dedicated logic, etc.), software (such as is run on a general-purpose computer system or a dedicated machine), firmware, or combinations thereof.

A dashboard is displayed (block 1202). The dashboard indicates clinicians who have performed ultrasound examinations and benchmarking data including one or more of ultrasound data generated as part of the ultrasound examinations, contextual data representing a context for the ultrasound examinations, scheduling data representing schedules for the ultrasound examinations, and reporting data representing medical reports generated for the ultrasound examinations. In an example, the dashboard displays clinicians on one axis of a grid (e.g., on a vertical axis) and benchmarking data on another axis of the grid (e.g., a horizontal axis) forming a table of the benchmarking data associated with the clinicians. A user selection is received (block 1204). The user selection indicates selected data, the selected data including at least one of the clinicians and at least one of the benchmarking data. A benchmarking report is generated based on the user selection (block 1206). A benchmarking report generator implemented by the ultrasound system can generate the benchmarking report. The benchmarking report is displayed (e.g., on a display device) and includes a comparison of the selected data across the ultrasound examinations.

In embodiments, the dashboard includes an option for remote monitoring and management of an ultrasound machine used in one or more of the ultrasound examinations. For example, a user may enable the option including to designate one or more ultrasound machines as reference ultrasound machines so that changes made to the reference ultrasound machines are propagated to other ultrasound machines. The dashboard can include a list of the other ultrasound machines with options to enable or disable the automatic update of these other ultrasound machines based on the update of a reference ultrasound machine.

In one example, the dashboard includes a telemedicine panel that enables collaboration among clinicians who may be remote relative to an ultrasound examination. Hence, the dashboard can include an option to invite a clinician to review the ultrasound data. Additionally or alternatively, the dashboard can include an option to accept a request from a clinician for review of the ultrasound data. For example, the request can come from a clinician who participates in a crowd-source data review and is connected to a network that indicates when new data is available on the system. The clinician may notice the ultrasound data from the ultrasound examination indicated as new data that fits the clinician's expertise. In response, the clinician may submit a request to view the ultrasound data so that they can provide their opinion.

In an example, the benchmarking report generator is implemented to obtain, based on the user selection, non-ultrasound imaging data. The benchmarking report generator can generate the benchmarking report including a visual representation that compares the ultrasound data of the benchmarking data to the non-ultrasound imaging data. For example, the non-ultrasound imaging data can include MRI and/or CT image data for a same patient as the ultrasound data. The ultrasound system can then obtain the MRI and/or CT data (e.g., from a medical archiver) and generate the visual representation to include both an ultrasound image and an MRI and/or CT image, such as side-by-side or overlaid on one another.

In embodiments, the user selection indicates at least one of: two or more ultrasound equipment manufacturers; two or more patients; two or more of the clinicians; two or more departments within a care facility; and two or more care facilities. Additionally or alternatively, the user selection can indicate a timeliness of the medical reports and one or more time intervals to quantify the timeliness. For instance, the user selection can indicate to report on the time of submissions of medical reports for ultrasound examinations and include time intervals in hours, such as within one hour, three hours, and eight hours of completion of the ultrasound examination. The benchmarking report can include a histogram indicating the number of medical reports submitted in accordance with the time intervals for the selected clinicians.

In one example, the dashboard includes results of at least one machine-learned model from processing, automatically and without user intervention, the ultrasound data. For example, the ultrasound system can, responsive to the ultrasound data being saved (e.g., on the ultrasound machine and/or on an archiver), process the ultrasound data with at least one machine-learned model. An example of a machine-learned model includes a convolutional neural network (CNN) trained to detect a pneumothorax condition for a patient's lungs. The dashboard can display an inference generated by the CNN, such as a probability of a pneumothorax condition. If the probability exceeds a threshold probability (e.g., 75%), the dashboard can display a warning.

FIG. 13 illustrates an example method 1300 that can be implemented by an ultrasound system in accordance with some embodiments. The ultrasound system can include an ultrasound scanner, an ultrasound machine, a processor system, a display device, and a synchronizer circuit. In some embodiments, the ultrasound system includes a wearable component, such as a patch with a transducer array. Operations of the method are performed by processing logic that can comprise hardware (circuitry, dedicated logic, etc.), software (such as is run on a general-purpose computer system or a dedicated machine), firmware, or combinations thereof.

A dashboard indicating a first data group and a second data group is displayed (block 1302). The first data group identifies at least one of clinicians having performed ultrasound examinations, patients having undergone the ultrasound examinations, care facilities where the ultrasound examinations were performed, departments of a care facility where the ultrasound examinations were performed, and ultrasound equipment used in the ultrasound examinations. The second data group identifies at least one of ultrasound data generated as part of the ultrasound examinations, contextual data representing a context for the ultrasound examinations, scheduling data representing schedules for the ultrasound examinations, and reporting data representing timeliness of medical reports generated for the ultrasound examinations.

A first user selection that indicates an element of the first data group and a second user selection that indicates an additional element of the second data group are received (block 1304). A benchmarking report is generated that includes a comparison of the element of the first data group for the additional element of the second data group (block 1306). In embodiments, the display device can display the benchmarking report on the dashboard.

In one example, the user input device receives a user input that selects a graph type, and the processor system generates the benchmarking report so that the comparison includes a graph according to the graph type. The user input device can receive an additional user input that selects a time scale, and the graph can include at least one axis based on the time scale. For example, the graph can have graduations on an axis that correspond to the time scale. The graph type can include a histogram, and the histogram can have bins corresponding to a one-hour time scale selected by the additional user input.

In embodiments, the user input device can receive a user input that indicates a distribution list, and the system can share the benchmarking report with one or more members on the distribution list. Additionally or alternatively, the user input device can receive an additional user input that indicates a distribution frequency, and the system can share the benchmarking report according to the distribution frequency, such as daily, weekly, monthly, quarterly, etc. Additionally or alternatively, the user input device can receive a user input that indicates a distribution method, and the system can communicate the benchmarking report for user consumption according to the distribution method, such as via email, for display on the dashboard, via text, via chat, etc.

In embodiments, the element includes at least one of the clinicians and the additional element includes the ultrasound data. Additionally or alternatively, the element can include at least one of the clinicians and the additional element can includes the contextual data. Additionally or alternatively, the element can include at least one of the clinicians and the additional element can include the scheduling data. Additionally or alternatively, the element can include at least one of the clinicians and the additional element can include the reporting data.

In embodiments, the element includes at least one of the patients and the additional element includes the ultrasound data. Additionally or alternatively, the element can include at least one of the patients and the additional element can include the contextual data. Additionally or alternatively, the element can include at least one of the patients and the additional element can include the scheduling data.

In embodiments, the element includes at least one of the care facilities and the additional element includes the ultrasound data. Additionally or alternatively, the element can include at least one of the care facilities and the additional element can include the contextual data. Additionally or alternatively, the element can include at least one of the care facilities and the additional element can include the scheduling data. Additionally or alternatively, the element can include at least one of the care facilities and the additional element can include the reporting data.

In embodiments, the element includes at least one of the departments and the additional element includes the ultrasound data. Additionally or alternatively, the element can include at least one of the departments and the additional element can include the contextual data. Additionally or alternatively, the element can include at least one of the departments and the additional element can include the scheduling data. Additionally or alternatively, the element can include at least one of the departments and the additional element can include the reporting data.

In embodiments, the element includes the ultrasound equipment and the additional element includes the ultrasound data. Additionally or alternatively, the element can include the ultrasound equipment and the additional element can include the contextual data. Additionally or alternatively, the element can include the ultrasound equipment and the additional element can include the reporting data.

FIG. 14 illustrates an example method 1400 that can be implemented by an ultrasound system in accordance with some embodiments. The ultrasound system can include an ultrasound scanner, an ultrasound machine, a processor system, a display device, and a synchronizer circuit. In some embodiments, the ultrasound system includes a wearable component, such as a patch with a transducer array. Operations of the method are performed by processing logic that can comprise hardware (circuitry, dedicated logic, etc.), software (such as is run on a general-purpose computer system or a dedicated machine), firmware, or combinations thereof.

A dashboard is displayed, the dashboard including a selection to enable remote management of ultrasound machines (block 1402). It is determined that one of the ultrasound machines has been updated with a configuration revision (block 1404). Responsive to the one of the ultrasound machines being updated and the selection being enabled, at least an additional one of the ultrasound machines is updated to include the configuration revision (block 1406).

In embodiments, the display device receives, via the dashboard, a user selection that designates the one of the ultrasound machines as a reference ultrasound machine whose updates are to be propagated to the ultrasound machines. Additionally or alternatively, the processor system can update, based on determining that one of the ultrasound machines has been updated with a configuration revision, the ultrasound machines so that they have matching configurations (e.g., the ultrasound machines are configured in a same manner, such as with same software revision numbers).

In embodiments, the processor system can determine that another of the ultrasound machines has been updated with an additional configuration revision. The processor system can then update, based on the configuration revision and the additional configuration revision, the ultrasound machines so that they have matching configurations.

In one example, the processor system generates a benchmarking report that compares the ultrasound machines and their configuration revisions when used to perform ultrasound examinations. For instance, the benchmarking report can include a list or table that depicts ultrasound examinations, including their types, the ultrasound machines, and their configurations when used to perform the ultrasound examinations. Hence, an administrator can track the propagation of configuration revisions and see what types of ultrasound examinations in which they are used. The display device can display the benchmarking report via the dashboard.

In an example, the configuration revision includes a patient list. The patient list can identify patients who had ultrasound examinations using the one of the ultrasound machines. Additionally or alternatively, the configuration revision can include an ultrasound protocol on the one of the ultrasound machines. Additionally or alternatively, the configuration revision can include an examination preset on the one of the ultrasound machines.

In embodiments, the display device can receive, via the dashboard, a user selection of an update frequency. The processor system can then schedule the update of the at least an additional one of the ultrasound machines based on the update frequency.

The systems, devices, and methods disclosed herein constitute numerous advantages over conventional systems, devices, and methods. The systems, devices, and methods disclosed herein can interpret ultrasound data based on contextual data, including regional data, environmental data, patient data, and clinician data, and uncover hidden correlations among features in these data groups. In contrast, conventional systems, devices, and methods do not interpret ultrasound data based on contextual data, so that the ultrasound data may be poorly or incorrectly interpreted. Moreover, the systems, devices, and methods disclosed herein facilitate patient-centric examinations and are not limited to study-centric examinations in which a patient's history is not considered and instead the study-centric examination is limited to data gathered during that examination. Consequently, the systems, devices, and methods disclosed herein result in an improved workflow with the ability to graph, at the point of care, patient data over time, providing for more-informed diagnoses and better patient care compared to conventional systems, devices, and methods. Further, the systems, devices, and methods disclosed herein can generate strategic-level reports to guarantee quality across a department, not just quality for a single examination. The reports provide for fast identification of low-quality data and underperforming operators. The systems, devices, and methods disclosed herein support future processing of data with techniques that were either not possible at the time the data was saved, or not implementable in real-time.

Example Device

Figure 15:
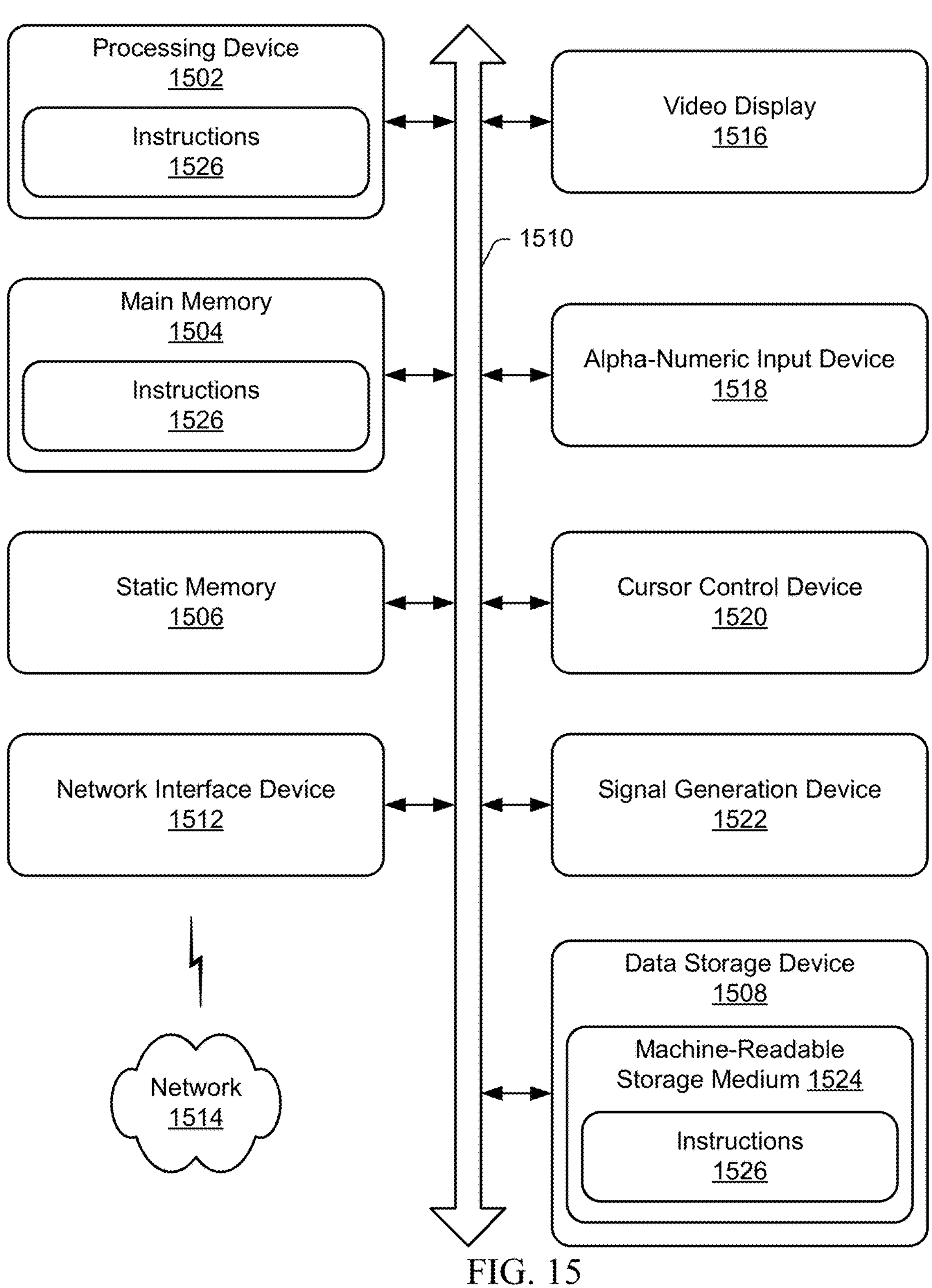
FIG. 15 illustrates a block diagram of an example computing device that can perform one or more of the operations described herein, in accordance with some embodiments.

FIG. 15 illustrates a block diagram of an example computing device 1500 that can perform one or more of the operations described herein, in accordance with some embodiments. The computing device 1500 can be connected to other computing devices in a local area network (LAN), an intranet, an extranet, and/or the Internet. The computing device can operate in the capacity of a server machine in a client-server network environment or in the capacity of a client in a peer-to-peer network environment. The computing device can be provided by a personal computer (PC), a server computer, a desktop computer, a laptop computer, a tablet computer, a smartphone, an ultrasound machine, or any machine capable of executing a set of instructions (sequential or otherwise) that specify actions to be taken by that machine. Further, while only a single computing device is illustrated, the term "computing device" shall also be taken to include any collection of computing devices that individually or jointly execute a set (or multiple sets) of instructions to perform the methods discussed herein. In some implementations, the computing device 1500 is one or more of an ultrasound machine, an ultrasound scanner, an access point, and a packet-forwarding component.

The example computing device 1500 can include a processing device 1502 (e.g., a general-purpose processor, a programmable logic device (PLD), etc.), a main memory 1504 (e.g., synchronous dynamic random-access memory (DRAM), read-only memory (ROM), etc.), and a static memory 1506 (e.g., flash memory, a data storage device 1508, etc.), which can communicate with each other via a bus 1510. The processing device 1502 can be provided by one or more general-purpose processing devices such as a microprocessor, a central processing unit, or the like. In an illustrative example, the processing device 1502 comprises a complex instruction set computing (CISC) microprocessor, a reduced instruction set computing (RISC) microprocessor, a very long instruction word (VLIW) microprocessor, or a processor implementing other instruction sets or processors implementing a combination of instruction sets. The processing device 1502 can also comprise one or more special-purpose processing devices such as an application-specific integrated circuit (ASIC), a field programmable gate array (FPGA), a digital signal processor (DSP), a network processor, or the like. The processing device 1502 can be configured to execute the operations described herein, in accordance with one or more aspects of the present disclosure, for performing the operations and steps discussed herein.

The computing device 1500 can further include a network interface device 1512, which can communicate with a network 1514. The computing device 1500 also can include a video display unit 1516 (e.g., a liquid crystal display (LCD), an organic light-emitting diode (OLED), a cathode ray tube (CRT), etc.), an alphanumeric input device 1518 (e.g., a keyboard), a cursor control device 1520 (e.g., a mouse), and an acoustic signal generation device 1522 (e.g., a speaker, a microphone, etc.). In one embodiment, the video display unit 1516, the alphanumeric input device 1518, and the cursor control device 1520 can be combined into a single component or device (e.g., an LCD touch screen).

The data storage device 1508 can include a computer-readable storage medium 1524 on which can be stored one or more sets of instructions 1526 (e.g., instructions for carrying out the operations described herein, in accordance with one or more aspects of the present disclosure). The instructions 1526 can also reside, completely or at least partially, within the main memory 1504 and/or within the processing device 1502 during execution thereof by the computing device 1500, where the main memory 1504 and the processing device 1502 also constitute computer-readable media. The instructions can further be transmitted or received over the network 1514 via the network interface device 1512.

Various techniques are described in the general context of software, hardware elements, or program modules. Generally, such modules include routines, programs, objects, elements, components, data structures, and so forth that perform particular tasks or implement particular abstract data types. The terms "module," "functionality," and "component" as used herein generally represent software, firmware, hardware, or a combination thereof. In some aspects, the modules described herein are embodied in the data storage device 1508 of the computing device 1500 as executable instructions or code. Although represented as software implementations, the described modules can be implemented as any form of a control application, software application, signal-processing and control module, hardware, or firmware installed on the computing device 1500.

While the computer-readable storage medium 1524 is shown in an illustrative example to be a single medium, the term "computer-readable storage medium" should be taken to include a single medium or multiple media (e.g., a centralized or distributed database and/or associated caches and servers) that store the one or more sets of instructions. The term "computer-readable storage medium" shall also be taken to include any medium that is capable of storing, encoding, or carrying a set of instructions for execution by the machine and that causes the machine to perform the methods described herein. The term "computer-readable storage medium" shall accordingly be taken to include, but not be limited to, solid-state memories, optical media, and magnetic media.

An Example Operating Environment

Figure 16:
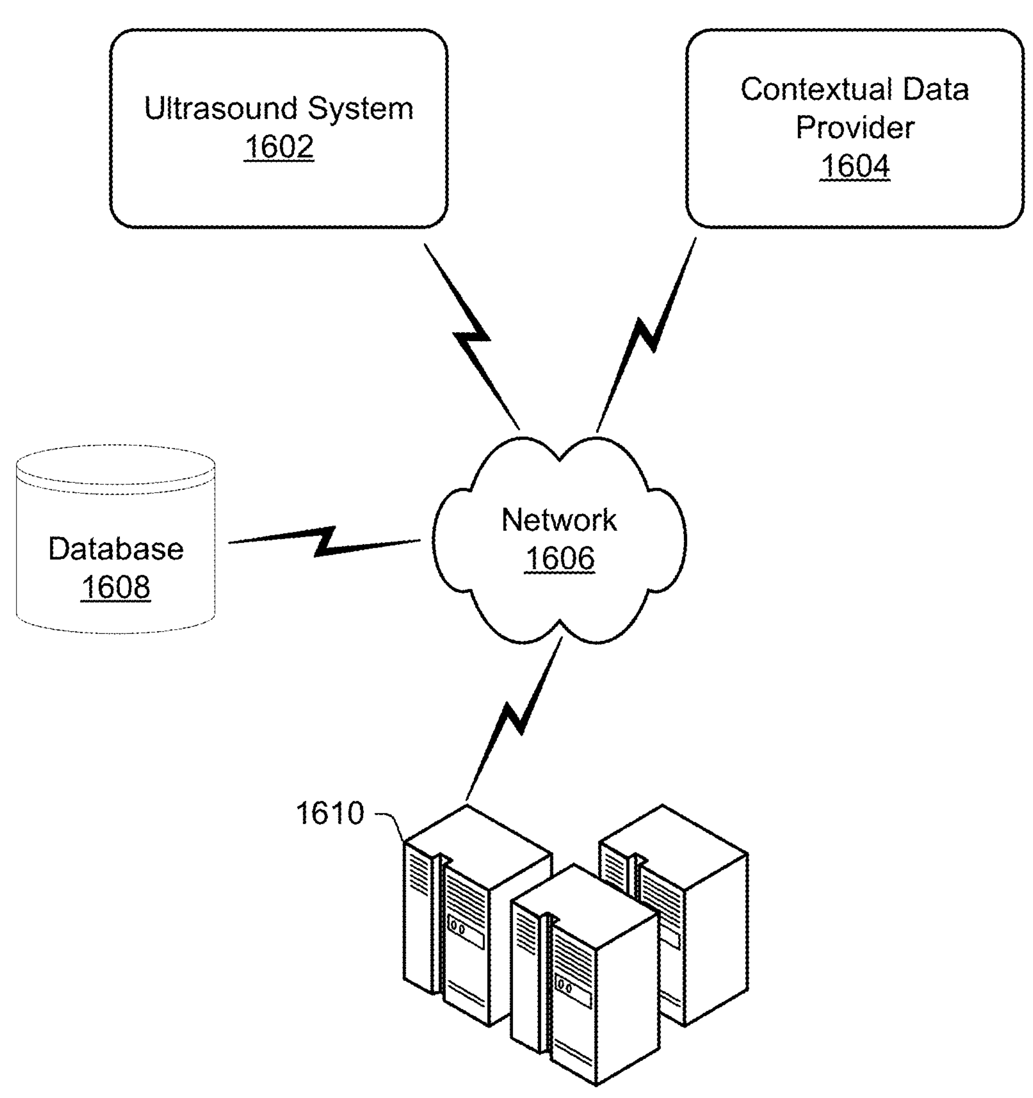
FIG. 16 illustrates an operating environment for an ultrasound system in accordance with some embodiments.

FIG. 16 illustrates an operating environment 1600 for an ultrasound system in accordance with some embodiments. The environment 1600 includes an ultrasound system 1602. Generally, the ultrasound system 1602 can include any suitable device (e.g., a component of an ultrasound system). Examples devices of the ultrasound system 1602 include a charging station, an ultrasound machine, a display device (e.g., a tablet or smartphone), an ultrasound scanner, and an ultrasound cart. Other examples include a transducer cable, a transducer cable holder, a docking station for an ultrasound machine, a scanner station configured to hold one or more ultrasound scanners, a needle guide, a battery for a wireless ultrasound scanner, a battery for an ultrasound machine, a registration system, and the like.

The environment 1600 also includes the contextual data provider 1604 that can provide contextual data for an ultrasound examination. In an example, the contextual data provider 1604 includes an entity that is separate from the care facility where ultrasound examinations are performed. For instance, the contextual data provider 1604 can include a news/event aggregator, weather source, traffic source, etc. Additionally or alternatively, the contextual data provider 1604 can include an entity related to the care facility where ultrasound examinations are performed. For instance, the contextual data provider 1604 can include an office or department of the care facility responsible for generating contextual data for events occurring in the care facility, such as a list of examinations scheduled, staff directory, equipment pool, etc.

The contextual data provider 1604 and the ultrasound system 1602 can be in communication via the network 1606 as part of the environment 1600. The network 1606 can include any suitable network, such as a local area network, a wide area network, a near field communication network, the Internet, an intranet, an extranet, a system bus that couples devices or device components (e.g., in an ASIC, FPGA, or SOC), and combinations thereof. Accordingly, in embodiments, information can be communicated to the ultrasound system 1602 and/or the contextual data provider 1604 through the network 1606. For instance, the database 1608 can store instructions executable by a processor system of the ultrasound system 1602 and communicate the instructions via the network 1606. The database 1608 can store contextual data provided by the contextual data provider 1604. In some embodiments, the database 1608 includes a medical records archiver that stores medical data for patients, including ultrasound data generated as part of an ultrasound examination.

The environment 1600 also includes a server system 1610 that can implement any of the functions described herein. The server system 1610 can be a separate device from the ultrasound system 1602. Alternatively, the server system 1610 can be included in at least one of the ultrasound system 1602. In some embodiments, the server system 1610 and the database 1608 are included in the ultrasound system 1602. In some embodiments, the server system 1610 is implemented as a remote server system that is remote from (e.g., not collocated with) the ultrasound system 1602.

The following examples pertain to further embodiments:

A system comprising an archiver configured to maintain benchmarking data for ultrasound examinations, the benchmarking data including one or more of ultrasound data generated as part of the ultrasound examinations, contextual data representing a context for the ultrasound examinations, scheduling data representing schedules for the ultrasound examinations, and reporting data representing medical reports generated for the ultrasound examinations; a computing device coupled to the archiver and configured to generate a benchmarking report that includes a comparison of the benchmarking data across the ultrasound examinations; and a display device coupled to the computing device and configured to display the benchmarking report including the comparison.

A system comprising an archiver configured to maintain benchmarking data for ultrasound examinations, the benchmarking data including one or more of ultrasound data generated as part of the ultrasound examinations, contextual data representing a context for the ultrasound examinations, scheduling data representing schedules for the ultrasound examinations, and reporting data representing medical reports generated for the ultrasound examinations; a computing device coupled to the archiver and configured to generate a benchmarking report that includes a comparison of the benchmarking data across the ultrasound examinations; and a display device coupled to the computing device and configured to display the benchmarking report including the comparison.

A system comprising an archiver configured to maintain benchmarking data for ultrasound examinations, the benchmarking data including one or more of ultrasound data generated as part of the ultrasound examinations, contextual data representing a context for the ultrasound examinations, scheduling data representing schedules for the ultrasound examinations, and reporting data representing medical reports generated for the ultrasound examinations; a computing device coupled to the archiver and configured to generate a benchmarking report that includes a comparison of the benchmarking data across the ultrasound examinations; and a display device coupled to the computing device and configured to display the benchmarking report including the comparison, wherein the benchmarking data includes the ultrasound data obtained from at least two ultrasound equipment manufacturers, and the benchmarking report includes a visual representation that compares the ultrasound data obtained from the at least two ultrasound equipment manufacturers.

A system comprising an archiver configured to maintain benchmarking data for ultrasound examinations, the benchmarking data including one or more of ultrasound data generated as part of the ultrasound examinations, contextual data representing a context for the ultrasound examinations, scheduling data representing schedules for the ultrasound examinations, and reporting data representing medical reports generated for the ultrasound examinations; a computing device coupled to the archiver and configured to generate a benchmarking report that includes a comparison of the benchmarking data across the ultrasound examinations; and a display device coupled to the computing device and configured to display the benchmarking report including the comparison, wherein the benchmarking data includes the reporting data for the medical reports generated by at least two clinicians who performed the ultrasound examinations, and the benchmarking report compares submission timeliness for the medical reports generated by the at least two clinicians.

A system comprising an archiver configured to maintain benchmarking data for ultrasound examinations, the benchmarking data including one or more of ultrasound data generated as part of the ultrasound examinations, contextual data representing a context for the ultrasound examinations, scheduling data representing schedules for the ultrasound examinations, and reporting data representing medical reports generated for the ultrasound examinations; a computing device coupled to the archiver and configured to generate a benchmarking report that includes a comparison of the benchmarking data across the ultrasound examinations; and a display device coupled to the computing device and configured to display the benchmarking report including the comparison, wherein archiver is implemented to obtain the benchmarking data from at least two departments within a care facility, and the benchmarking report compares the at least two departments based on the benchmarking data.

A system comprising an archiver configured to maintain benchmarking data for ultrasound examinations, the benchmarking data including one or more of ultrasound data generated as part of the ultrasound examinations, contextual data representing a context for the ultrasound examinations, scheduling data representing schedules for the ultrasound examinations, and reporting data representing medical reports generated for the ultrasound examinations; a computing device coupled to the archiver and configured to generate a benchmarking report that includes a comparison of the benchmarking data across the ultrasound examinations; and a display device coupled to the computing device and configured to display the benchmarking report including the comparison, wherein archiver is implemented to obtain the benchmarking data from at least two departments within a care facility, and the benchmarking report compares the at least two departments based on the benchmarking data, wherein the benchmarking data includes the scheduling data that indicates numbers of the ultrasound examinations performed within the at least two departments, and the comparison indicates the numbers of the ultrasound examinations.

A system comprising an archiver configured to maintain benchmarking data for ultrasound examinations, the benchmarking data including one or more of ultrasound data generated as part of the ultrasound examinations, contextual data representing a context for the ultrasound examinations, scheduling data representing schedules for the ultrasound examinations, and reporting data representing medical reports generated for the ultrasound examinations; a computing device coupled to the archiver and configured to generate a benchmarking report that includes a comparison of the benchmarking data across the ultrasound examinations; and a display device coupled to the computing device and configured to display the benchmarking report including the comparison, wherein archiver is implemented to obtain the benchmarking data from at least two departments within a care facility, and the benchmarking report compares the at least two departments based on the benchmarking data, wherein the benchmarking data includes the scheduling data that indicates types of the ultrasound examinations performed within the at least two departments, and the comparison indicates the types of the ultrasound examinations.

A system comprising an archiver configured to maintain benchmarking data for ultrasound examinations, the benchmarking data including one or more of ultrasound data generated as part of the ultrasound examinations, contextual data representing a context for the ultrasound examinations, scheduling data representing schedules for the ultrasound examinations, and reporting data representing medical reports generated for the ultrasound examinations; a computing device coupled to the archiver and configured to generate a benchmarking report that includes a comparison of the benchmarking data across the ultrasound examinations; and a display device coupled to the computing device and configured to display the benchmarking report including the comparison, wherein archiver is implemented to obtain the benchmarking data from at least two care facilities, and the benchmarking report compares the at least two care facilities based on the benchmarking data.

A system comprising an archiver configured to maintain benchmarking data for ultrasound examinations, the benchmarking data including one or more of ultrasound data generated as part of the ultrasound examinations, contextual data representing a context for the ultrasound examinations, scheduling data representing schedules for the ultrasound examinations, and reporting data representing medical reports generated for the ultrasound examinations; a computing device coupled to the archiver and configured to generate a benchmarking report that includes a comparison of the benchmarking data across the ultrasound examinations; and a display device coupled to the computing device and configured to display the benchmarking report including the comparison, wherein archiver is implemented to obtain the benchmarking data including the scheduling data that indicates scheduled times for when the ultrasound examinations were scheduled to occur and actual times for when the ultrasound examinations did occur, and the comparison indicates differences between the scheduled times and the actual times.

A system comprising an archiver configured to maintain benchmarking data for ultrasound examinations, the benchmarking data including one or more of ultrasound data generated as part of the ultrasound examinations, contextual data representing a context for the ultrasound examinations, scheduling data representing schedules for the ultrasound examinations, and reporting data representing medical reports generated for the ultrasound examinations; a computing device coupled to the archiver and configured to generate a benchmarking report that includes a comparison of the benchmarking data across the ultrasound examinations; and a display device coupled to the computing device and configured to display the benchmarking report including the comparison, wherein at least one of the computing device and the display device is implemented to receive a user input indicating report times, and the display device is implemented to obtain and display the benchmarking report according to the report times.

A system comprising an archiver configured to maintain benchmarking data for ultrasound examinations, the benchmarking data including one or more of ultrasound data generated as part of the ultrasound examinations, contextual data representing a context for the ultrasound examinations, scheduling data representing schedules for the ultrasound examinations, and reporting data representing medical reports generated for the ultrasound examinations; a computing device coupled to the archiver and configured to generate a benchmarking report that includes a comparison of the benchmarking data across the ultrasound examinations; and a display device coupled to the computing device and configured to display the benchmarking report including the comparison, wherein at least one of the computing device and the display device is implemented to receive a user input indicating a selection of the benchmarking data to include in the comparison included in the benchmarking report.

A system comprising an archiver configured to maintain benchmarking data for ultrasound examinations, the benchmarking data including one or more of ultrasound data generated as part of the ultrasound examinations, contextual data representing a context for the ultrasound examinations, scheduling data representing schedules for the ultrasound examinations, and reporting data representing medical reports generated for the ultrasound examinations; a computing device coupled to the archiver and configured to generate a benchmarking report that includes a comparison of the benchmarking data across the ultrasound examinations; and a display device coupled to the computing device and configured to display the benchmarking report including the comparison, wherein at least one of the computing device and the display device is implemented to receive a user input indicating a delivery method of the benchmarking report to the display device.

A system comprising an archiver configured to maintain benchmarking data for ultrasound examinations, the benchmarking data including one or more of ultrasound data generated as part of the ultrasound examinations, contextual data representing a context for the ultrasound examinations, scheduling data representing schedules for the ultrasound examinations, and reporting data representing medical reports generated for the ultrasound examinations; a computing device coupled to the archiver and configured to generate a benchmarking report that includes a comparison of the benchmarking data across the ultrasound examinations; and a display device coupled to the computing device and configured to display the benchmarking report including the comparison, wherein at least one of the computing device and the display device is implemented to receive a user input indicating a delivery method of the benchmarking report to the display device, wherein the delivery method includes at least one of email delivery and access via a benchmarking application configured to display a dashboard.

A computing device comprising a display device configured to display a dashboard indicating clinicians having performed ultrasound examinations and benchmarking data including one or more of ultrasound data generated as part of the ultrasound examinations, contextual data representing a context for the ultrasound examinations, scheduling data representing schedules for the ultrasound examinations, and reporting data representing medical reports generated for the ultrasound examinations; a user input device configured to receive a user selection that indicates selected data, the selected data including at least one of the clinicians and at least one of the benchmarking data; and a benchmarking report generator configured to generate, based on the user selection, a benchmarking report that includes a comparison of the selected data across the ultrasound examinations, the display device configured to display the benchmarking report.

A computing device comprising a display device configured to display a dashboard indicating clinicians having performed ultrasound examinations and benchmarking data including one or more of ultrasound data generated as part of the ultrasound examinations, contextual data representing a context for the ultrasound examinations, scheduling data representing schedules for the ultrasound examinations, and reporting data representing medical reports generated for the ultrasound examinations; a user input device configured to receive a user selection that indicates selected data, the selected data including at least one of the clinicians and at least one of the benchmarking data; and a benchmarking report generator configured to generate, based on the user selection, a benchmarking report that includes a comparison of the selected data across the ultrasound examinations, the display device configured to display the benchmarking report, wherein the dashboard includes an option for remote monitoring and management of an ultrasound machine used in one or more of the ultrasound examinations.

A computing device comprising a display device configured to display a dashboard indicating clinicians having performed ultrasound examinations and benchmarking data including one or more of ultrasound data generated as part of the ultrasound examinations, contextual data representing a context for the ultrasound examinations, scheduling data representing schedules for the ultrasound examinations, and reporting data representing medical reports generated for the ultrasound examinations; a user input device configured to receive a user selection that indicates selected data, the selected data including at least one of the clinicians and at least one of the benchmarking data; and a benchmarking report generator configured to generate, based on the user selection, a benchmarking report that includes a comparison of the selected data across the ultrasound examinations, the display device configured to display the benchmarking report, wherein the dashboard includes an option to invite a clinician to review the ultrasound data.

A computing device comprising a display device configured to display a dashboard indicating clinicians having performed ultrasound examinations and benchmarking data including one or more of ultrasound data generated as part of the ultrasound examinations, contextual data representing a context for the ultrasound examinations, scheduling data representing schedules for the ultrasound examinations, and reporting data representing medical reports generated for the ultrasound examinations; a user input device configured to receive a user selection that indicates selected data, the selected data including at least one of the clinicians and at least one of the benchmarking data; and a benchmarking report generator configured to generate, based on the user selection, a benchmarking report that includes a comparison of the selected data across the ultrasound examinations, the display device configured to display the benchmarking report, wherein the dashboard includes an option to accept a request from a clinician for review of the ultrasound data.

A computing device comprising a display device configured to display a dashboard indicating clinicians having performed ultrasound examinations and benchmarking data including one or more of ultrasound data generated as part of the ultrasound examinations, contextual data representing a context for the ultrasound examinations, scheduling data representing schedules for the ultrasound examinations, and reporting data representing medical reports generated for the ultrasound examinations; a user input device configured to receive a user selection that indicates selected data, the selected data including at least one of the clinicians and at least one of the benchmarking data; and a benchmarking report generator configured to generate, based on the user selection, a benchmarking report that includes a comparison of the selected data across the ultrasound examinations, the display device configured to display the benchmarking report, wherein the benchmarking report generator is implemented to obtain, based on the user selection, non-ultrasound imaging data, and generate the benchmarking report including a visual representation that compares the ultrasound data of the benchmarking data to the non-ultrasound imaging data.

A computing device comprising a display device configured to display a dashboard indicating clinicians having performed ultrasound examinations and benchmarking data including one or more of ultrasound data generated as part of the ultrasound examinations, contextual data representing a context for the ultrasound examinations, scheduling data representing schedules for the ultrasound examinations, and reporting data representing medical reports generated for the ultrasound examinations; a user input device configured to receive a user selection that indicates selected data, the selected data including at least one of the clinicians and at least one of the benchmarking data; and a benchmarking report generator configured to generate, based on the user selection, a benchmarking report that includes a comparison of the selected data across the ultrasound examinations, the display device configured to display the benchmarking report, wherein the user selection indicates at least one of: two or more ultrasound equipment manufacturers; two or more patients; two or more of the clinicians; two or more departments within a care facility; and two or more care facilities.

A computing device comprising a display device configured to display a dashboard indicating clinicians having performed ultrasound examinations and benchmarking data including one or more of ultrasound data generated as part of the ultrasound examinations, contextual data representing a context for the ultrasound examinations, scheduling data representing schedules for the ultrasound examinations, and reporting data representing medical reports generated for the ultrasound examinations; a user input device configured to receive a user selection that indicates selected data, the selected data including at least one of the clinicians and at least one of the benchmarking data; and a benchmarking report generator configured to generate, based on the user selection, a benchmarking report that includes a comparison of the selected data across the ultrasound examinations, the display device configured to display the benchmarking report, wherein the user selection indicates a timeliness of the medical reports and one or more time intervals to quantify the timeliness.

A computing device comprising a display device configured to display a dashboard indicating a first data group and a second data group, the first data group identifying at least one of clinicians having performed ultrasound examinations, patients having undergone the ultrasound examinations, care facilities where the ultrasound examinations were performed, departments of a care facility where the ultrasound examinations were performed, and ultrasound equipment used in the ultrasound examinations, the second data group identifying at least one of ultrasound data generated as part of the ultrasound examinations, contextual data representing a context for the ultrasound examinations, scheduling data representing schedules for the ultrasound examinations, and reporting data representing timeliness of medical reports generated for the ultrasound examinations; a user input device configured to receive a first user selection that indicates an element of the first data group and a second user selection that indicates an additional element of the second data group; and a processor system configured to generate a benchmarking report that includes a comparison of the element of the first data group for the additional element of the second data group.

Unless specifically stated otherwise, terms such as “transmitting,” “determining,” “receiving,” “generating,” “or the like, refer to actions and processes performed or implemented by computing devices that manipulates and transforms data represented as physical (electronic) quantities within the computing device's registers and memories into other data similarly represented as physical quantities within the computing device memories or registers or other such information storage, transmission or display devices. Also, the terms “first,” “second,” “third,” “fourth,” etc., as used herein are meant as labels to distinguish among different elements and may not necessarily have an ordinal meaning according to their numerical designation.

Examples described herein also relate to an apparatus for performing the operations described herein. This apparatus may be specially constructed for the required purposes, or it may comprise a general-purpose computing device selectively programmed by a computer program stored in the computing device. Such a computer program may be stored in a computer-readable non-transitory storage medium, such as a storage memory.

The methods and illustrative examples described herein are not inherently related to any particular computer or other apparatus. Various general-purpose systems may be used in accordance with the teachings described herein, or it may prove convenient to construct more specialized apparatus to perform the methods. The structure for a variety of these systems will appear as set forth in the description above.

The above description is intended to be illustrative, and not restrictive. Although the present disclosure has been described with references to specific illustrative examples, it will be recognized that the present disclosure is not limited to the examples described. The scope of the disclosure should be determined with reference to the following claims, along with the full scope of equivalents to which the claims are entitled.

As used herein, the singular forms “a”, “an” and “the” are intended to include the plural forms as well, unless the context clearly indicates otherwise. It will be further understood that the terms “comprises”, “comprising”, “includes”, and/or “including”, when used herein, specify the presence of stated features, integers, steps, operations, elements, and/or components, but do not preclude the presence or addition of one or more other features, integers, steps, operations, elements, components, and/or groups thereof. Therefore, the terminology used herein is for the purpose of describing particular embodiments only and is not intended to be limiting.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Although the method operations were described in a specific order, it should be understood that other operations may be performed in between described operations, described operations may be adjusted so that they occur at slightly different times or the described operations may be distributed in a system which allows the occurrence of the processing operations at various intervals associated with the processing.

Various units, circuits, or other components may be described or claimed as “configured to” or “configurable to” perform a task or tasks. In such contexts, the phrase “configured to” or “configurable to” is used to connote structure by indicating that the units/circuits/components include structure (e.g., circuitry) that performs the task or tasks during operation. As such, the unit/circuit/component can be said to be configured to perform the task, or configurable to perform the task, even when the specified unit/circuit/component is not currently operational (e.g., is not on). The units/circuits/components used with the “configured to” or “configurable to” language include hardware—for example, circuits, memory storing program instructions executable to implement the operation, etc. Reciting that a unit/circuit/component is “configured to” perform one or more tasks, or is “configurable to” perform one or more tasks, is expressly intended not to invoke 35 U.S.C. 112, sixth paragraph, for that unit/circuit/component.

Additionally, “configured to” or “configurable to” can include generic structure (e.g., generic circuitry) that is manipulated by software and/or firmware (e.g., an FPGA or a general-purpose processor executing software) to operate in manner that is capable of performing the task(s) at issue. “Configured to” may also include adapting a manufacturing process (e.g., a semiconductor fabrication facility) to fabricate devices (e.g., integrated circuits) that are adapted to implement or perform one or more tasks. “Configurable to” is expressly intended not to apply to blank media, an unprogrammed processor or unprogrammed generic computer, or an unprogrammed programmable logic device, programmable gate array, or other unprogrammed device, unless accompanied by programmed media that confers the ability to the unprogrammed device to be configured to perform the disclosed function(s).

Reference in the specification to “one embodiment”, “an embodiment”, “one example”, or “an example” means that a particular feature, structure, or characteristic described in conjunction with the embodiment can be included in at least one embodiment. The appearances of the phrases “in one embodiment” or “in an embodiment” in various places in the specification do not necessarily all refer to the same embodiment. The processes depicted in the figures that follow are performed by processing logic that comprises hardware (e.g., circuitry, dedicated logic, etc.), software, or a combination of both. Although the processes are described below in terms of some sequential operations, it should be appreciated that some of the operations described may be performed in a different order. Moreover, some operations may be performed in parallel rather than sequentially.

In the specification, the term “and/or” describes three relationships between objects that may exist. For example, A and/or B may represent the following cases: only A exists, both A and B exist, and only B exist, where A and B may be singular or plural.

The foregoing description, for the purpose of explanation, has been described with reference to specific embodiments. However, the illustrative discussions above are not intended to be exhaustive or to limit embodiments of the invention to the precise forms disclosed. Many modifications and variations are possible in view of the above teachings. The embodiments were chosen and described in order to best explain the principles of the embodiments and its practical applications, to thereby enable others skilled in the art to best utilize the embodiments and various modifications as may be suited to the particular use contemplated. Accordingly, the present embodiments are to be considered as illustrative and not restrictive, and are not to be limited to the details given herein, but may be modified within the scope and equivalents of the appended claims.

What is claimed is:

1. An ultrasound system comprising:

an ultrasound scanner configured to transmit ultrasound at a patient anatomy and generate ultrasound data as part of an ultrasound examination;

an ultrasound machine configured to generate, based on the ultrasound data, an ultrasound image; and a processor system implemented to:

determine features selected from the group consisting of regional features, patient features, clinician features, and ultrasound examination features;

determine a feature vector including the features selected from the group consisting of regional features, patient features, clinician features, and ultrasound examination features; and generate, based on the ultrasound image and the feature vector, a patient recommendation, wherein the processor system is implemented to generate, based on the ultrasound image and the feature vector, an audit report that compares the ultrasound examination and an additional ultrasound examination.

2. The ultrasound system as described in claim 1, wherein the processor system implements:

a neural network to generate, based on the ultrasound image, an inference for the patient anatomy; and an additional neural network to receive the inference and the feature vector and generate the patient recommendation based on the inference and the feature vector.

3. The ultrasound system as described in claim 1, wherein at least one of the features is unavailable during the ultrasound examination.

4. The ultrasound system as described in claim 1, wherein the patient recommendation includes at least one of an additional examination, a clinical trial, and a medication.

5. The ultrasound system as described in claim 1, further comprising a display device, wherein the processor system is implemented to obtain an additional ultrasound image generated during an additional ultrasound examination, wherein the display device is implemented to simultaneously display the ultrasound image and the additional ultrasound image.

6. The ultrasound system as described in claim 1, further comprising a display device and a synchronizer circuit, wherein the ultrasound machine is implemented to generate a video clip that includes the ultrasound image, wherein the processor system is implemented to obtain an additional video clip of ultrasound images, wherein the synchronizer circuit is implemented to synchronize the video clip and the additional video clip and the display device is implemented to simultaneously and synchronously display the video clip and the additional video clip.

7. The ultrasound system as described in claim 1, further comprising a display device, wherein the processor system is implemented to:

obtain an additional ultrasound image generated during a previous ultrasound examination; and generate a first segmentation of the patient anatomy from the ultrasound image and a second segmentation of the patient anatomy from the additional ultrasound image, wherein the display device is implemented to display the first segmentation and the second segmentation.

8. The ultrasound system as described in claim 1, further comprising a display device implemented to display a user interface configured to:

display a value measured from the patient anatomy in the ultrasound image;

receive a user selection of the value; and display, responsive to the user selection, the ultrasound image.

9. The ultrasound system as described in claim 1, wherein the features include the regional features, and the regional features include at least one of a population size, a population density, a pollution level, a number of airports, a zip code, and a regional news event in the region where the ultrasound examination is performed.

10. The ultrasound system as described in claim 1, wherein the features include the patient features, and the patient features include at least one of a patient age, a patient weight, a symptom description, patient genomic data, and a patient medical history.

11. The ultrasound system as described in claim 1, wherein the features include the clinician features, and the clinician features include at least one of a clinician age, an education level, a number of ultrasound examinations performed, and an amount of time since a vacation.

12. The ultrasound system as described in claim 1, wherein the features include the ultrasound examination features, and the ultrasound examination features include at least one of cleaning data for the ultrasound system, calibration data for the ultrasound system, radio frequency measurements obtained during the ultrasound examination, indicators of equipment proximate to the ultrasound system during the ultrasound examination, weather during the ultrasound examination, a time of day of the ultrasound examination, and a day of week of the ultrasound examination.

13. A method to control an ultrasound system, comprising:

transmitting, using an ultrasound scanner, ultrasound at a patient anatomy and generating ultrasound data as part of an ultrasound examination;

generating, using an ultrasound machine, an ultrasound image based on the ultrasound data;

determining, using a processor system, features selected from the group consisting of regional features, patient features, clinician features, and ultrasound examination features;

determining, using the processor system, a feature vector including the features selected from the group consisting of regional features, patient features, clinician features, and ultrasound examination features;

generating, using the processor system, a patient recommendation based on the ultrasound image and the feature vector; and generating, using the processor system, an audit report that compares the ultrasound examination and an additional ultrasound examination based on the ultrasound image and the feature vector.

14. The method as described in claim 13, further comprising:

generating, using a neural network, an inference for the patient anatomy based on the ultrasound image;

receiving, using an additional neural network, the inference and the feature vector; and generating, using the additional neural network, the patient recommendation based on the inference and the feature vector.

15. The method as described in claim 13, further comprising:

generating, using the ultrasound machine, a video clip that includes the ultrasound image, obtaining, using the processor system, an additional video clip of ultrasound images synchronizing, using a synchronizer circuit, the video clip and the additional video clip; and simultaneously and synchronously displaying, using the processor system, the video clip and the additional video clip on a display device.

16. The method as described in claim 13, further comprising:

obtaining, using the processor system, an additional ultrasound image generated during a previous ultrasound examination; and generating, using the processor system, a first segmentation of the patient anatomy from the ultrasound image and a second segmentation of the patient anatomy from the additional ultrasound image; and displaying, using the processor system, the first segmentation and the second segmentation on a display device.

17. The method as described in claim 13, further comprising:

displaying, using the processor system, a user interface on a display device;

displaying, using the processor system, a value measured from the patient anatomy in the ultrasound image on the display device;

receiving, using the processor system, a user selection of the value; and displaying, using the processor system, the ultrasound image responsive to the user selection.

18. The method as described in claim 13, wherein the regional features include at least one of a population size, a population density, a pollution level, a number of airports, a zip code, and a regional news event, the patient features include at least one of a patient age, a patient weight, a symptom description, patient genomic data, and a patient medical history, the clinician features include at least one of a clinician age, an education level, a number of ultrasound examinations performed, and an amount of time since a vacation, and the ultrasound examination features include at least one of cleaning data for the ultrasound system, calibration data for the ultrasound system, radio frequency measurements obtained during the ultrasound examination, indicators of equipment proximate to the ultrasound system during the ultrasound examination, weather during the ultrasound examination, a time of day of the ultrasound examination, and a day of week of the ultrasound examination.

19. The method as described in claim 13, further comprising:

obtaining, using the processor system, an additional ultrasound image generated during an additional ultrasound examination; and simultaneously displaying, using a display device, the ultrasound image and the additional ultrasound image.

20. The method as described in claim 13, wherein the patient recommendation includes at least one of an additional examination, a clinical trial, and a medication.

* * * * *